(12) United States Patent
Yamada

(10) Patent No.: US 8,842,900 B2
(45) Date of Patent: Sep. 23, 2014

(54) SPECIMEN PROCESSING SYSTEM AND BLOOD CELL IMAGE CLASSIFYING APPARATUS

(75) Inventor: Kazuhiro Yamada, Kobe (JP)

(73) Assignee: Sysmex Corporation, Hyogo (JP)

( * ) Notice: Subject to any disclaimer, the term of this patent is extended or adjusted under 35 U.S.C. 154(b) by 527 days.

(21) Appl. No.: 12/606,645

(22) Filed: Oct. 27, 2009

(65) Prior Publication Data
US 2010/0104169 A1    Apr. 29, 2010

(30) Foreign Application Priority Data

Oct. 28, 2008 (JP) ................................. 2008-277503
Oct. 28, 2008 (JP) ................................. 2008-277504

(51) Int. Cl.
*G06K 9/00* (2006.01)
*G01N 15/14* (2006.01)
*G01N 35/00* (2006.01)
*G01N 15/00* (2006.01)

(52) U.S. Cl.
CPC ...... *G06K 9/00127* (2013.01); *G01N 2015/008* (2013.01); *G01N 15/1429* (2013.01); *G01N 2015/1486* (2013.01); *G01N 35/0092* (2013.01); *G01N 35/00584* (2013.01)
USPC ............................ 382/133; 382/128; 382/134

(58) Field of Classification Search
None
See application file for complete search history.

(56) References Cited

U.S. PATENT DOCUMENTS

| | | | | |
|---|---|---|---|---|
| 5,270,212 A | * | 12/1993 | Horiuchi et al. ................. | 436/45 |
| 5,365,559 A | * | 11/1994 | Hsueh et al. ..................... | 377/10 |
| 5,548,395 A | * | 8/1996 | Kosaka .............................. | 356/73 |
| 5,677,183 A | | 10/1997 | Takarada | |
| 5,804,448 A | * | 9/1998 | Wang et al. ....................... | 436/63 |
| 5,880,835 A | * | 3/1999 | Yamazaki et al. ............. | 356/336 |
| 6,317,511 B1 | * | 11/2001 | Horiuchi ........................ | 382/133 |
| 6,922,479 B2 | * | 7/2005 | Berliner ......................... | 382/134 |
| 7,361,472 B2 | * | 4/2008 | Yguerabide et al. ............ | 435/7.1 |
| 2002/0001402 A1 | * | 1/2002 | Berliner ......................... | 382/133 |
| 2006/0250604 A1 | * | 11/2006 | Hamada et al. .................. | 356/39 |
| 2007/0243523 A1 | * | 10/2007 | Ionescu-Zanetti et al. ....... | 435/4 |
| 2008/0201082 A1 | | 8/2008 | Tohma et al. | |
| 2008/0279441 A1 | * | 11/2008 | Matsuo et al. ................. | 382/133 |
| 2008/0317325 A1 | * | 12/2008 | Ortyn et al. .................... | 382/133 |
| 2009/0015831 A1 | * | 1/2009 | Yguerabide et al. .......... | 356/337 |
| 2010/0054575 A1 | * | 3/2010 | Zhou et al. .................... | 382/134 |
| 2010/0284602 A1 | * | 11/2010 | Winkelman et al. .......... | 382/134 |

FOREIGN PATENT DOCUMENTS

| | | | | | |
|---|---|---|---|---|---|
| CN | WO2008/046292 | * | 4/2008 | ............. | G01N 33/49 |
| JP | 60-162955 A | | 8/1985 | | |
| JP | 05-080045 A | | 3/1993 | | |

(Continued)

*Primary Examiner* — Avinash J Yentrapati
(74) *Attorney, Agent, or Firm* — Sughrue Mion, PLLC

(57) ABSTRACT

A specimen processing system comprising: a blood cell counting apparatus; and a blood cell image classifying apparatus, wherein the blood cell image classifying apparatus comprises a controller to carry out operations, comprising: receiving a plurality of first count results of a predetermined type of the blood cell by the blood cell counting apparatus; obtaining a plurality of second count results of the predetermined type of the blood cell on the basis of the blood cell image; storing the plurality of the first count results and the second count results; reading at least one of the first count results, and at least one of the second count results obtained from a blood specimen corresponding to the first count result; generating and outputting a quality control screen on the basis of the read first count result and the read second count result. A blood cell image classifying apparatus is also disclosed.

16 Claims, 35 Drawing Sheets

(56) References Cited

FOREIGN PATENT DOCUMENTS

| JP | 07-055693 | 3/1995 |
| JP | 2000-258335 | 9/2000 |
| JP | 2002-365285 A | 12/2002 |

\* cited by examiner

FIG.8A

| SPECIMEN ID | Neut | Eosin | Baso | ... | WBC SCATTERGRAM ABNORMALITY | NRBC SCATTERGRAM ABNORMALITY | NEUTROPENIA ABNORMALITY | ... | MEASUREMENT DATE |
|---|---|---|---|---|---|---|---|---|---|
| 00001 | 75.2 | 1.2 | 1.5 | ... | 0 | 0 | 0 | ... | 2008/9/1 |
| 00002 | 70.3 | 1.8 | 1.2 | ... | 0 | 1 | 0 | ... | 2008/9/1 |
| 00003 | 79.7 | 0.8 | 0.4 | ... | 1 | 0 | 0 | ... | 2008/9/2 |
| ... | ... | ... | ... | ... | ... | ... | ... | ... | ... |

SPECIMEN ID = 0003

FIG.9

| BLOOD CELL TYPE | REVIEW |
|---|---|
| Band | YES |
| Seg | YES |
| Eosin | NO |
| Baso | YES |
| ⋮ | ⋮ |

SPECIMEN PROCESSING SYSTEM AND BLOOD CELL IMAGE CLASSIFYING APPARATUS

FIELD OF THE INVENTION

The present invention relates to a specimen processing system that is provided with a blood cell counting apparatus which measures a blood specimen and counts blood cells for each type, and a blood cell image classifying apparatus which is connected to the blood cell counting apparatus so as to perform data communication therewith and counts the blood cells for each type on the basis of the blood cell image obtained by imaging a blood smear, and to a blood cell image classifying apparatus.

BACKGROUND

Blood cell image classifying apparatuses are known which image blood smears and classify blood cells into red blood cells, white blood cells, a subclass of the white blood cells, and the like on the basis of the obtained blood cell image (for example, JP-A-2002-365285). In addition, in this kind of blood cell image classifying apparatus, a technique is also known in which the blood cell image classifying apparatus is connected to a blood cell counting apparatus, which aspirates the blood specimen and measures the aspirated blood specimen to classify and count the blood cells on the basis of optical information, so as to perform data communication therewith (for example, JP-A-5-80045).

The blood cell counting apparatus periodically measures a quality control specimen which includes a predetermined amount of red blood cells, white blood cells and the like, and confirms that correct analysis results are being obtained, that is, quality control is typically performed. On the other hand, in the known blood cell image classifying apparatus described above, even though a quality control scheme exists, there is a need for classifying the blood cell images and confirming that the count results thus obtained for each type of blood cell are correct on the basis of a highly reliable reference value.

SUMMARY OF THE INVENTION

The scope of the present invention is defined solely by the appended claims, and is not affected to any degree by the statements within this summary.

A first aspect of the present invention is a specimen processing system comprising: a blood cell counting apparatus for counting blood cells for each type by measuring a blood specimen; and a blood cell image classifying apparatus, which is connected to the blood cell counting apparatus so as to perform data communication therewith, for counting the blood cells for each type on the basis of a blood cell image obtained by imaging a blood smear, wherein the blood cell image classifying apparatus comprises a controller including a memory under control of a processor, the memory storing instructions enabling the processor to carry out operations, comprising: receiving a plurality of first count results of a predetermined type of the blood cell by the blood cell counting apparatus; obtaining a plurality of second count results of the predetermined type of the blood cell on the basis of the blood cell image; storing the plurality of the first count results and the plurality of the second count results; reading at least one of the first count results, and at least one of the second count results obtained from a blood specimen corresponding to the first count result; generating a quality control screen on the basis of the read first count result and the read second count result; and outputting the quality control screen.

A second aspect of the present invention is a blood cell image classifying apparatus which is connected to a blood cell counting apparatus for counting blood cells for each type by measuring a blood specimen, so as to perform data communication therewith, comprising: an imaging section for obtaining a blood cell image by imaging a blood smear; and a controller including a memory under control of a processor, the memory storing instructions enabling the processor to carry out operations, comprising: receiving a plurality of first count results of a predetermined type of the blood cell by the blood cell counting apparatus; obtaining a plurality of second count results of the predetermined type of the blood cell on the basis of the blood cell image; storing the plurality of the first count results and the plurality of the second count result; reading at least one of the first count results, and at least one of the second count results obtained from a blood specimen corresponding to the first count result; generating a quality control screen on the basis of the read first count result and the read second count result; and outputting the quality control screen.

A third aspect of the present invention is a specimen processing system comprising: a blood cell counting apparatus for counting blood cells for each type by measuring a blood specimen; and a blood cell image classifying apparatus, which is connected to the blood cell counting apparatus so as to perform data communication therewith, for counting the blood cells for each type on the basis of a blood cell image obtained by imaging a blood smear, wherein the blood cell image classifying apparatus comprises a controller including a memory under control of a processor, the memory storing instructions enabling the processor to carry out operations, comprising: receiving a first count result of a predetermined type of the blood cells by the blood cell counting apparatus; obtaining a second count result of the predetermined type of the blood cells on the basis of the blood cell image; comparing the first count result with the second count result which is obtained from a blood specimen corresponding to the first count result; and outputting a warning when the difference between the first count result and the second count result exceeds a predetermined range.

A fourth aspect of the present invention is a blood cell image classifying apparatus which is connected to a blood cell counting apparatus for counting blood cells for each type by measuring a blood specimen, so as to perform data communication therewith, comprising: an imaging section for obtaining a blood cell image by imaging a blood smear; and a controller including a memory under control of a processor, the memory storing instructions enabling the processor to carry out operations, comprising: counting the blood cells for each type on the basis of the blood cell image which is obtained by imaging the blood smear; receiving a first count result of a predetermined type of the blood cells by the blood cell counting apparatus; obtaining a second count result of the predetermined type of the blood cells on the basis of the blood cell image; comparing the first count result with the second count result which is obtained from a blood specimen corresponding to the first count result; and outputting a warning when the difference between the first count result and the second count result exceeds a predetermined range.

BRIEF DESCRIPTION OF THE DRAWINGS

FIG. 8A is a schematic diagram showing the configuration of a specimen database;

FIG. 9 is a schematic diagram showing the data structure of a review item setting table;

DETAILED DESCRIPTION OF THE PREFERRED EMBODIMENTS

The preferred embodiments of the present invention will be described hereinafter with reference to the drawings.

This embodiment is a specimen analyzing system which images stained blood smears magnified by a microscope, classifies and counts the obtained blood cell images, and displays a quality control screen (accuracy management screen: "a quality control" is also called as "an accuracy management" hereinafter) of the count result.

[Configuration of Specimen Analyzing System]

Figure 1:
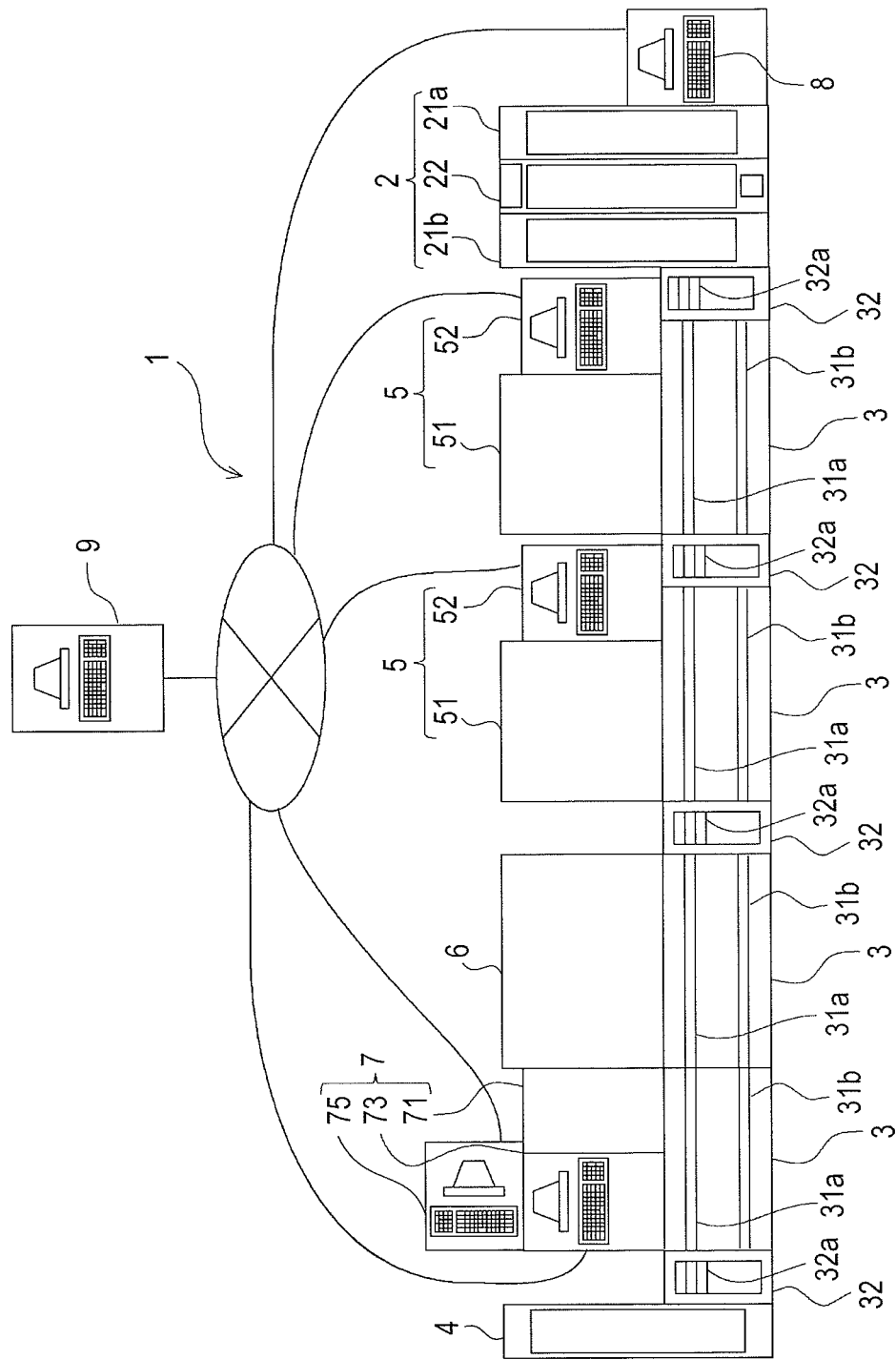
FIG. 1 is a schematic plan view showing the entire configuration of a specimen analyzing system according to an embodiment.

FIG. 1 is a schematic plan view showing the entire configuration of a specimen analyzing system according to this embodiment. As shown in FIG. 1, a specimen analyzing system 1 includes a specimen loading apparatus 2, specimen transport apparatuses 3, a specimen accommodating apparatus 4, blood cell counting apparatuses 5, a smear preparing apparatus 6, a blood cell image classifying apparatus 7 and a system control apparatus 8. The specimen analyzing system 1 according to this embodiment is connected to a host computer 9 via a communication network so as to communicate therewith.

<Configuration of Specimen Loading Apparatus 2>

The specimen loading apparatus 2 includes two specimen delivery units 21a and 21b and a bar-code reading unit 22 disposed between the two specimen delivery units 21a and 21b. The specimen delivery units 21a and 21b of the specimen loading apparatus 2 are configured to place sample racks each storing a plurality of specimen containers. The sample racks placed in the specimen delivery unit 21a are sequentially delivered to the bar-code reading unit 22. By means of the bar-code reading unit 22, rack IDs are read from bar-codes of bar-code labels adhered to the sample racks and specimen IDs are read from bar-codes of bar-code labels adhered to the specimen containers, and the rack IDs and the specimen IDs are transmitted to the system control apparatus 8. The sample rack for which the bar-code reading has been completed is transported to the specimen delivery unit 21b and from there transported to the specimen transport apparatus 3.

<Configuration of Specimen Transport Apparatus 3>

Next, the configuration of the specimen transport apparatus 3 will be described. As shown in FIG. 1, the specimen analyzing system 1 includes 4 specimen transport apparatuses 3. The specimen transport apparatuses 3, 3, 3 and 3 are disposed in front of the blood cell counting apparatuses 5 and 5, the smear preparing apparatus 6 and the blood cell image classifying apparatus 7, respectively. The neighboring specimen transport apparatuses 3 and 3 are connected to each other so as to be able to send and receive a sample rack to each other. The rightmost specimen transport apparatus 3 is connected to the above-described specimen loading apparatus 2 so as to be able to introduce the sample rack conveyed from the specimen loading apparatus 2. The leftmost specimen transport apparatus 3 is connected to the specimen accommodating apparatus 4 so as to be able to convey the sample rack to the specimen accommodating apparatus 4.

Rack sliders 32, 32 and 32 are respectively provided between the specimen loading apparatus 2 and the rightmost specimen transport apparatus 3 (the specimen transport apparatus 3 disposed in front of the blood cell counting apparatus 5 on the right side of the drawing) in FIG. 1, between the rightmost specimen transport apparatus 3 described immediately above and the specimen transport apparatus 3 (the specimen transport apparatus 3 disposed in front of the blood cell counting apparatus 5 on the left side of the drawing) disposed on the immediate left side of the rightmost specimen transport apparatus, and between the specimen transport apparatus 3 described immediately above and the specimen transport apparatus 3 (the specimen transport apparatus 3 disposed in front of the smear preparing apparatus 6 disposed on the immediate left side of the specimen transport apparatus 3 described immediately above.

The specimen transport apparatus 3 is provided with two rack transport paths 31a and 31b extending in a horizontal direction. The rack transport path 31a at the rear side is a measuring line for transporting a sample rack accommodating a specimen to be supplied to the blood cell counting apparatus 5 or the smear preparing apparatus 6. The rack transport path 31b at the front side is a skip line for transporting a sample rack not accommodating a specimen to be supplied to the blood cell counting apparatus 5 or the smear preparing apparatus 6.

The rack slider 32 is disposed on the right side of the specimen transport apparatus 3 to sort and put sample racks into the measuring line 31a and the skip line 31b of the specimen transport apparatus 3. The rack slider 32 includes one movable transport path and the movable transport path can be moved in a front-back direction by a motor (not shown).

In addition, the specimen transport apparatus 3 includes a rack bar-code reader and a specimen bar-code reader (not shown) which are capable of reading a rack ID and a specimen ID. Moreover, the specimen transport apparatus 3 is connected to the system control apparatus 8 so as to communicate therewith and is configured to receive a measuring order from the system control apparatus 8. A control section of the specimen transport apparatus 3 determines whether a specimen to be supplied to the blood cell counting apparatus 5 or the smear preparing apparatus 6 is accommodated in a sample rack on the basis of the measuring data provided from the system control apparatus 8 and the rack ID read by the bar-code reader. When a sample rack accommodating the specimen to be supplied to the blood cell counting apparatus 5 or the smear preparing apparatus 6 is introduced into the rack slider 32, a movable transport path 32a is moved to the rear to deliver the sample rack to the measuring line 31a. When a sample rack not accommodating the specimen to be supplied to the blood cell counting apparatus 5 or the smear preparing apparatus 6 is introduced into the rack slider 32, the movable transport path 32a is moved to the front to deliver the sample rack to the skip line 31b. That is, a sample rack accommodating only a specimen which is not an analysis object of the blood cell counting apparatus 5 is transported to the skip line 31b in the specimen transport apparatus 3 disposed in front of the blood cell counting apparatus 5, and a sample rack accommodating only a specimen which is not a smear preparation object of the smear preparing apparatus 6 is transported to the skip line 31b in the specimen transport apparatus 3 disposed in front of the smear preparing apparatus 6. When a sample rack accommodates any specimen, which is an analysis object of the blood cell counting apparatus 5, the sample rack is transported to the measuring line 31a in the specimen transport apparatus 3 disposed in front of the blood cell counting apparatus 5.

When a sample rack is delivered to the measuring line 31a, the control section of the specimen transport apparatus 3 repeats an operation of: moving a specimen container which is an object of analysis (smear preparing process) to an aspiration position where the blood cell counting apparatus 5 (smear preparing apparatus 6) aspirates a specimen; and moving a specimen container which is the next analysis object (object for smear preparing process) to the aspiration position after the blood cell counting apparatus 5 (smear preparing apparatus 6) completes the aspiration of the specimen.

<Configuration of Specimen Accommodating Apparatus 4>

The specimen accommodating apparatus 4 receives the sample rack, in which the analysis or smear preparing is completed, from the specimen transport apparatus 3, and accommodates the sample rack. Since the configuration of the specimen accommodating apparatus is the same as those of the specimen delivery units 21a and 21b, description thereof will be omitted.

<Configuration of Blood Cell Counting Apparatus 5>

The blood cell counting apparatus 5 as an optical flow cytometry type multiple blood cell counting apparatus obtains the fluorescent intensity, the side-scattered light intensity and the like of blood cells included in a blood specimen, classifies the blood cells included in the specimen on the basis of the above intensities, and counts the number of blood cells for each type. Moreover, the blood cell counting apparatus 5 creates a scattergram in which the classified blood cells are color-coded for each type, and displays the scattergram. The blood cell counting apparatus 5 includes a measuring unit 51 for measuring a blood specimen and an information processing unit 52 for processing measuring data output from the measuring unit 51 and displaying an analysis result of the blood specimen. As the blood cell counting apparatus 5, for example, XE-2100 (which is made by SYSMEX CO. Ltd.), LH700 series (which is made by BECKMAN COULTER CO. Ltd.), CELL DYN (which is made by ABBOTT CO. Ltd.), ADVIA (which is made by SIEMENS) or the like can be used.

Figure 2:
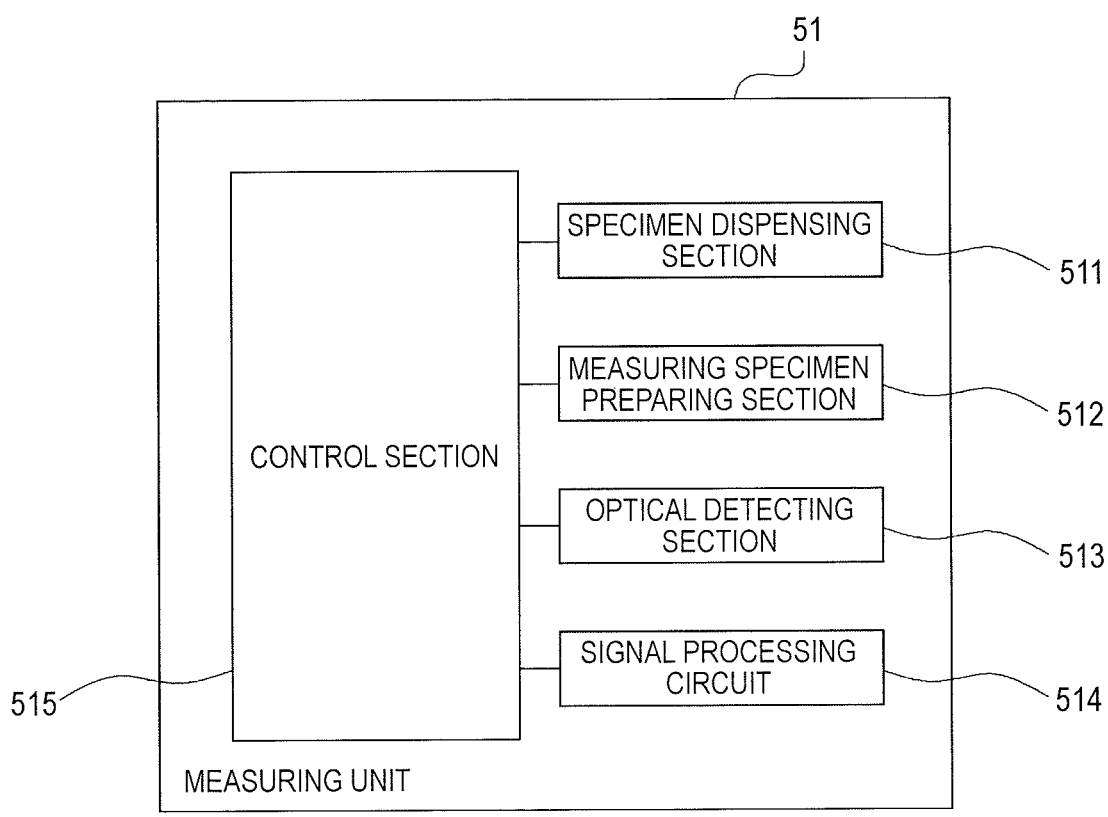
FIG. 2 is block diagram showing the schematic configuration of a measuring unit provided in the blood cell counting apparatus according to the embodiment.

FIG. 2 is a block diagram showing the schematic configuration of the measuring unit 51. The measuring unit 51 includes a specimen dispensing section 511, a measuring specimen preparing section 512, an optical detecting section 513, a signal processing circuit 514 and a control section 515.

The specimen dispensing section 511 includes an aspiration tube (not shown) and the aspiration tube is stuck into the cap section of a specimen container in the sample rack transported on the measuring line 31a of the specimen transport apparatus 3 to aspirate a blood specimen from the specimen container. The measuring specimen preparing section 512 includes a mixing container (not shown) to mix and stir the blood specimen dispensed by the specimen dispensing section 511, a reagent and a diluent and prepares a measuring specimen.

The optical detecting section 513 includes a flow cell (not shown) to form a narrow flow of the measuring specimen by supplying the measuring specimen to the flow cell and exposes the measuring specimen to light to obtain a side-scattered light signal, a forward-scattered light signal and a fluorescent signal by means of an optical sensor. These signals are output to the signal processing circuit 514. The signal processing circuit 514 processes an electric signal output from the optical detecting section 513. The signal processing circuit 514 obtains parameters such as peaks and pulse widths of the side-scattered light signal, the forward-scattered light signal and the fluorescent signal.

The control section 515 includes a CPU and a memory, and is connected to the specimen transport apparatus 3 so as to perform data communication therewith. The control section 515 controls the specimen dispensing section 511, the measuring specimen preparing section 512, the optical detecting section 513 and the signal processing circuit 514 in accordance with an analysis item provided from the specimen transport apparatus 3, and performs a measurement operation corresponding to the analysis item. In addition, the control section is configured to transmit measuring data including the parameters obtained by the signal processing circuit 514 to the information processing unit 52.

Figure 3:
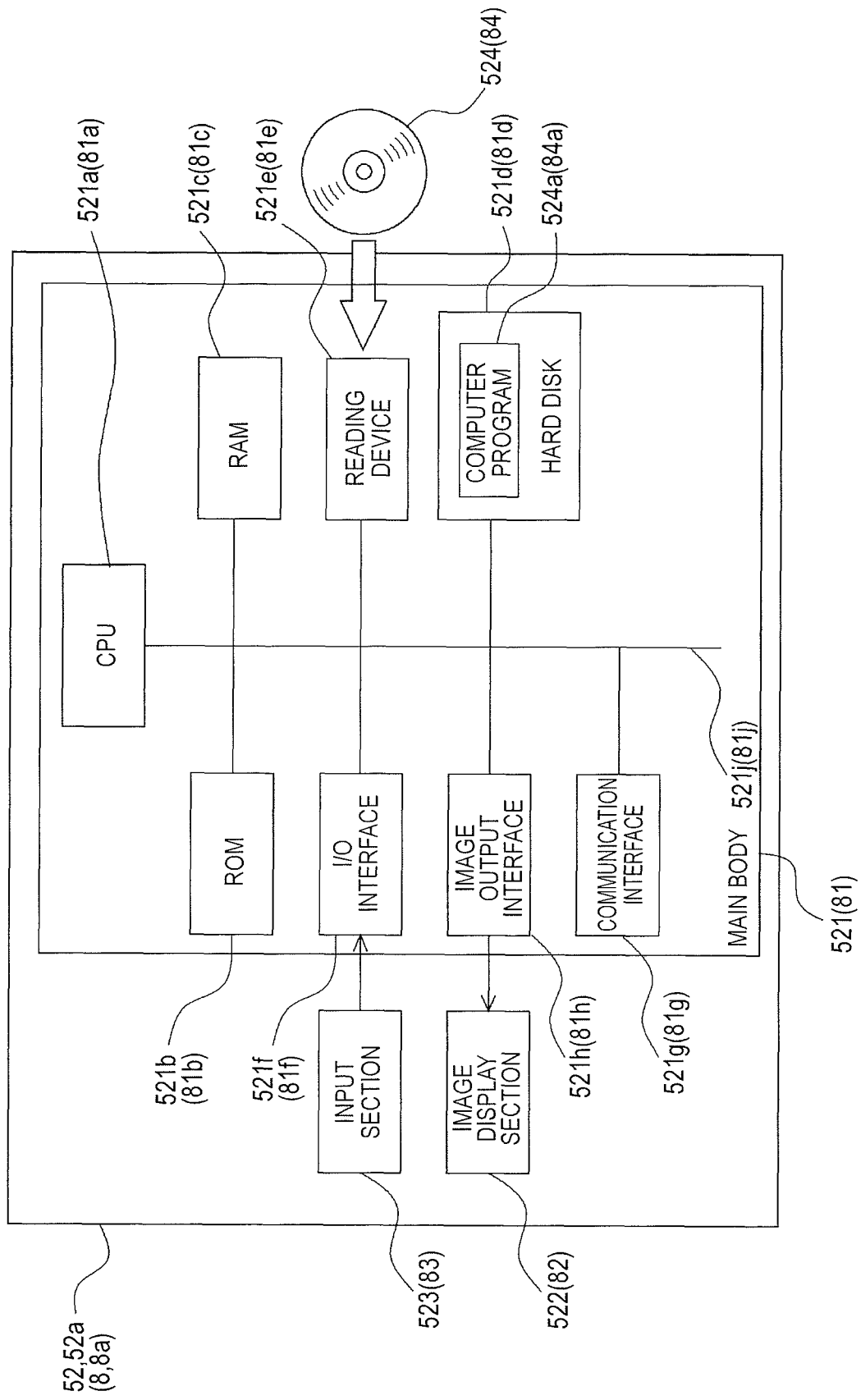
FIG. 3 is a block diagram showing the configuration of an information processing unit provided in the blood cell counting apparatus according to the embodiment.

Next, the configuration of the information processing unit 52 will be described. The information processing unit 52 is composed of a computer. FIG. 3 is a block diagram showing the configuration of the information processing unit 52. The information processing unit 52 is realized by a computer 52a. As shown in FIG. 3, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes an analysis program 524a to be described later, so that the computer 52a functions as the information processing unit 52.

The ROM 521b is composed of a mask ROM, a PROM, an EPROM, an EEPROM or the like and the computer program which is executed by the CPU 521a, data which is used for the computer program and the like are recorded in the ROM.

The RAM 521c is composed of an SRAM, a DRAM or the like. The RAM 521c is used to read the analysis program 524a recorded in the hard disk 521d. Moreover, the RAM is used as an operating area of the CPU 521a when the CPU 521a executes a computer program.

In the hard disk 521d, various computer programs for being executed by the CPU 521a, such as an operating system and an application program, and data which are used to execute the computer programs are installed. The analysis program 524a to be described later is also installed in the hard disk 521d.

The reading device 521e is composed of a flexible disk drive, a CD-ROM drive, a DVD-ROM drive or the like and can read the computer program or data recorded in a portable recording medium 524. In the portable recording medium 524, the analysis program 524a for prompting the computer to function as the information processing unit 52 is stored.

The computer 52a can read the analysis program 524a from the portable recording medium 524 and install the analysis program 524a in the hard disk 521d.

The analysis program 524a is provided by the portable recording medium 524 and can be also provided from an external device, which is connected to the computer 52a by an electric communication line (which may be wired or wireless) so as to communicate therewith, through the electric communication line. For example, the analysis program 524a is stored in a hard disk of a server computer on the internet and the computer 52a accesses the server computer to download the computer program and install the computer program in the hard disk 521d.

Furthermore, in the hard disk 521d, for example, a multi-tasking operating system such as Windows (registered trade name), which is made and distributed by Microsoft corporation in America, is installed. In the following description, the analysis program 524a according to this embodiment operates on the above operating system.

The I/O interface 521f is composed of, for example, a serial interface such as USB, IEEE1394 or RS-232C, a parallel interface such as SCSI, IDE or IEEE1284, and an analog interface including a D/A converter and an A/D converter. The input section 523 composed of a keyboard and a mouse is connected to the I/O interface 521f and a user can use the input section 523 to input data to the computer 52a.

The communication interface 521g is an Ethernet (registered trade name) interface. The communication interface 521g is connected to the measuring unit 51 via a LAN. Via the communication interface 521g, the computer 52a can send and receive data to and from the measuring unit 51 connected to the LAN by using a predetermined communication protocol. In addition, the communication interface 521g is connected to the host computer 9 via the LAN so as to communicate therewith.

The image output interface 521h is connected to the image display section 522 composed of a LCD, a CRT or the like to output a picture signal corresponding to the image data provided from the CPU 521a to the image display section 522. The image display section 522 displays an image (screen) in accordance with an input picture signal.

<Configuration of Smear Preparing Apparatus 6>

The smear preparing apparatus 6 aspirates a blood specimen so as to deliver it onto a slide glass in drops, spreads and dries the blood specimen on the slide glass, and supplies a stain solution to the slide glass to stain the blood on the slide glass. In this manner, the smear preparing apparatus prepares a smear.

Figure 4:
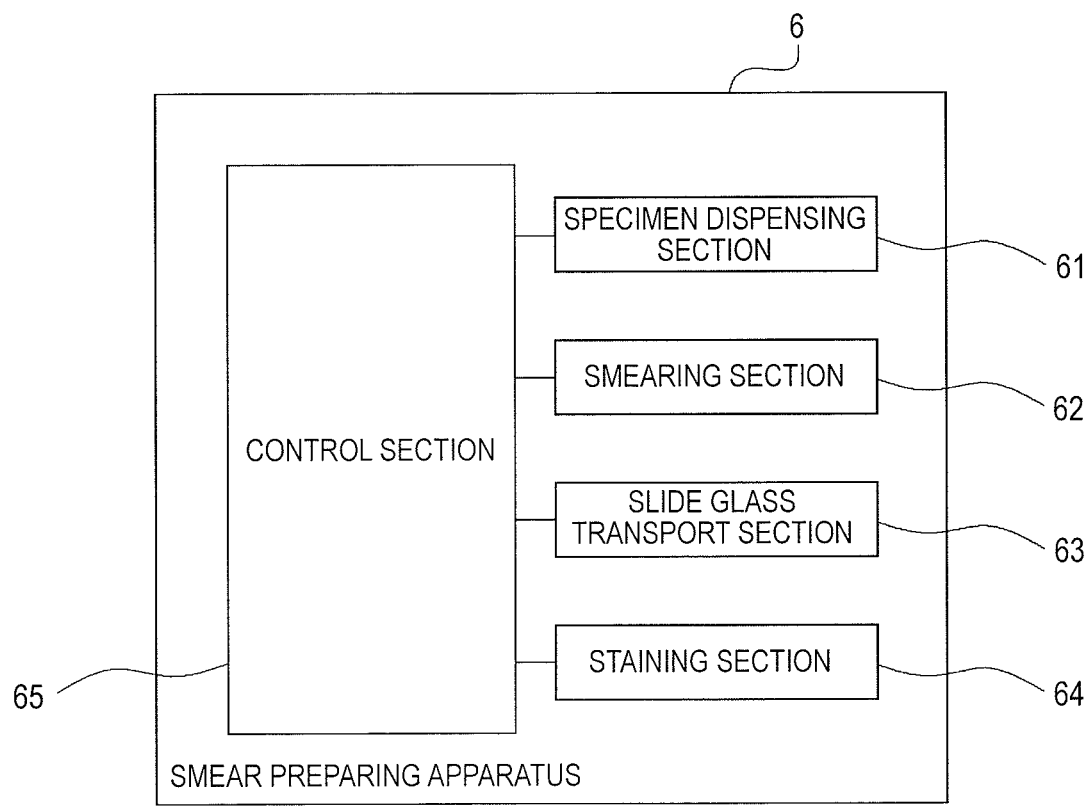
FIG. 4 is a block diagram showing the schematic configuration of a smear preparing apparatus according to the embodiment.

FIG. 4 is a block diagram showing the schematic configuration of the smear preparing apparatus 6. As shown in FIG. 4, the smear preparing apparatus 6 includes a specimen dispensing section 61, a smearing section 62, a slide glass transport section 63, a staining section 64 and a control section 65.

The specimen dispensing section 61 includes an aspiration tube (not shown) and the aspiration tube is stuck into the cap section of a specimen container in the sample rack transported on the measuring line 31a of the specimen transport apparatus 3 to aspirate a blood specimen from the specimen container. The specimen dispensing section 61 is configured to drop the aspirated blood specimen onto a slide glass. The smearing section 62 is configured to smear and dry the blood specimen dropped onto the slide glass and perform printing on the slide glass.

The slide glass transport section 63 is provided to accommodate the slide glass on which the blood specimen is smeared by the smearing section 62 in a cassette (not shown) and to transport the cassette. The staining section 64 supplies a stain solution to the slide glass in the cassette transported to a staining position by the slide glass transport section 63. The control section 65 controls the specimen dispensing section 61, the smearing section 62, the slide glass transport section 63 and the staining section 64 in accordance with a smear preparing instruction issued from the specimen transport apparatus 3 so as to perform the above smear preparing operation. The smear prepared in this manner is delivered to the blood cell image classifying apparatus 7.

<Configuration of Blood Cell Image Classifying Apparatus 7>

Figure 5:
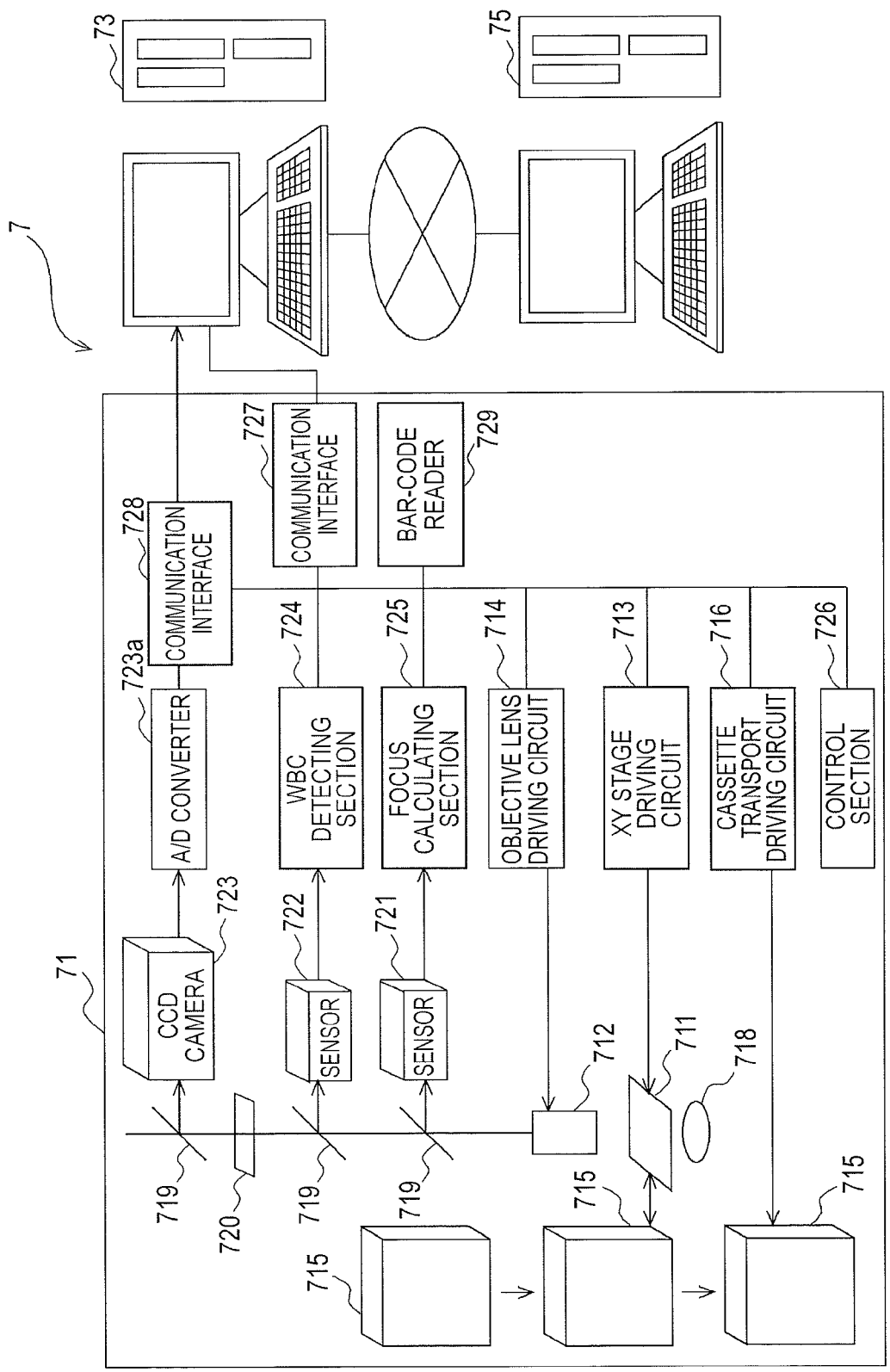
FIG. 5 is a block diagram showing the configuration of a blood cell image display apparatus according to the embodiment.

FIG. 5 is a block diagram showing the configuration of the blood cell image classifying apparatus according to this embodiment. FIG. 5 schematically shows the configuration of the apparatus. The arrangement of sensors, a slide cassette and the like may be slightly different from the actual arrangement to enable an easier understanding. For example, in FIG. 5, a sensor for WBC detection and a sensor for auto-focusing are respectively arranged on the upper and lower sides. However, in fact, as shown in FIG. 6 to be described later, both of the sensors are arranged in substantially the same plane.

The blood cell image classifying apparatus 7 includes a microscope unit 71 for imaging a magnified image of a blood smear which is focused by auto-focusing, an image processing unit 73 for processing a captured image to classify white blood cells in blood and performing a count operation for each classification of the white blood cell, and a blood cell image display unit 75 which is connected to the image processing unit 73 and displays the captured image, analysis results and the like. The image processing unit 73 and the blood cell image display unit 75 may be formed integrally, and not separately, with each other. The above-described smear preparing apparatus 6 (for example, a smear preparing apparatus SP-1000i made by Sysmex Corporation) is disposed near the blood cell image classifying apparatus 7 and a blood smear prepared by the smear preparing apparatus 6 is automatically supplied to the microscope unit 71.

<Configuration of Microscope Unit 71>

Figure 6:
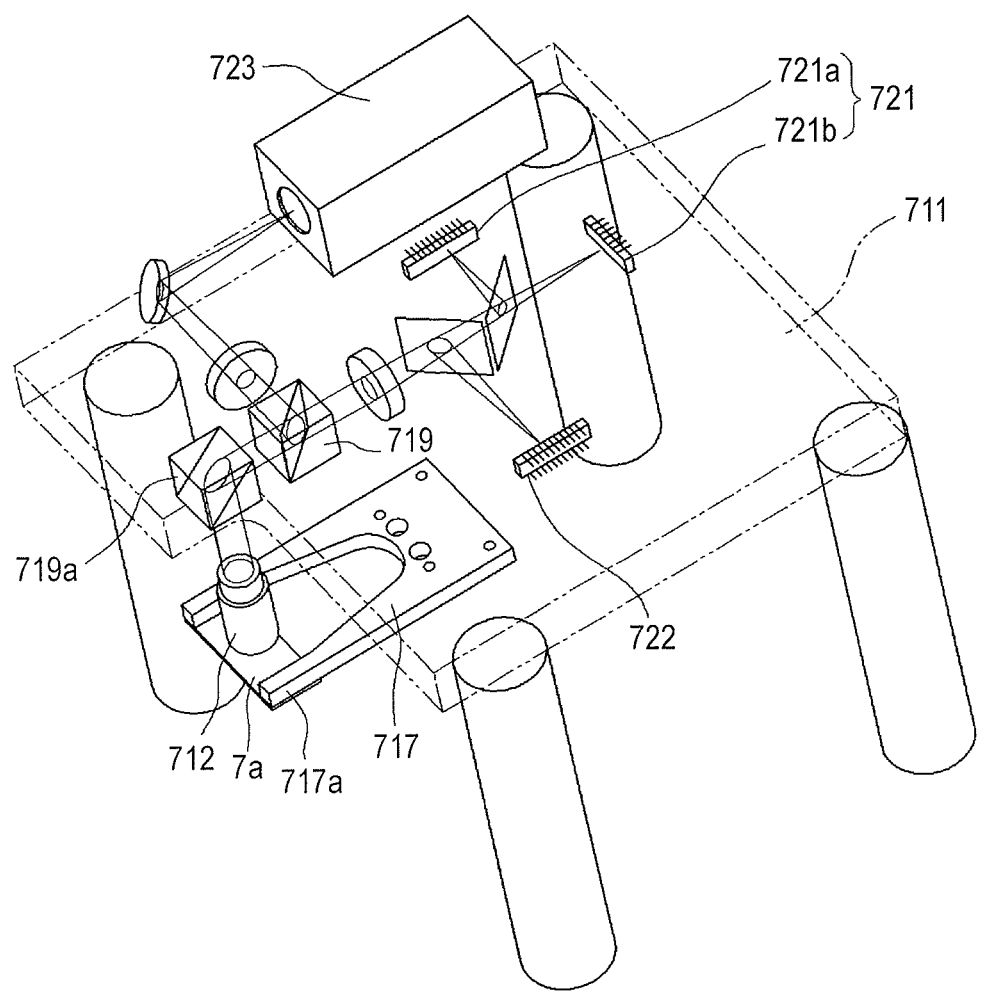
FIG. 6 is a perspective view showing a portion of the configuration of a microscope unit provided in the blood cell image display apparatus according to the embodiment.

FIG. 6 is a perspective view showing a portion of the microscope unit 71. The microscope unit 71 includes an objective lens 712 which is a portion of a lens system of a microscope magnifying an image of blood thinly spread and applied over a slide glass 7a mounted on an XY stage 711. The XY stage 711 holding a sample (the slide glass 7a with an upper surface on which the blood is smeared) can be moved back and forth and from side to side (X and Y directions) by a driving section (not shown), the driving of which is controlled by an XY stage driving circuit 713 (see FIG. 5 for reference). The objective lens 712 can be moved up and down (Z direction) by a driving section (not shown), the driving of which is controlled by an objective lens driving circuit 714.

A plurality of the slide glasses 7a are stacked and accommodated in a slide cassette 715. The slide cassette 715 is transported by a transporting section (not shown) which is controlled by a cassette transport driving circuit 716 so as to be driven. The XY stage 711 is provided with a chuck section 717 (see FIG. 6 for reference) capable of holding two parts in the vicinities of both ends in the longitudinal direction of the slide glass 7a, and the chuck section can be freely advanced and retracted with respect to the slide glass 7a accommodated in the slide cassette 715 which is stopped at a predetermined position. The chuck section 717 is advanced toward the slide cassette 715 to hold the slide glass 7a by an opening-closing operation of claw sections 717a which can be freely opened and closed and each of which is formed at the tip of the chuck section 717. Then, the chuck section 717 is retracted to draw the slide glass 7a from the slide cassette 715 so that the slide glass can be disposed at a predetermined position on the XY stage 711.

A lamp 718 as a light source is disposed below the slide glass 7a, and light from the lamp 718 passes through the blood on the slide glass 7a, and via half mirrors 719 and an interference filter 720 arranged on an optical path, enters a line sensor 721 for auto-focusing in which plural pixels are arranged in a line, a sensor 722 for white blood cell (WBC) detection in which plural pixels are arranged in a line and a CCD camera 723. A white blood cell detecting section 724 composed of FPGA, ASIC or the like is connected to the sensor 722 for white blood cell detection and is set up to provide the output signal of the sensor 722 to the white blood cell detecting section 724. A focus calculating section 725 composed of FPGA, ASIC or the like is connected to the sensor 721 for auto-focusing and is set up to provide the output signal of the sensor 721 to the focus calculating section 725. White blood cell detection is performed by the white blood cell detection section 724 on the basis of an output signal in accordance with the incident light of the sensor 722. Information to be used for the auto-focus operation is calculated by the focus calculating section 725 on the basis of an output signal in accordance with the incident light of the sensor 721. The auto-focus operation is performed on the basis of the information.

In addition, the microscope unit 71 includes a control section 726 and communication interfaces 727 and 728. The control section 726 includes a CPU and a memory, and is connected to the XY stage driving circuit 713, the objective lens driving circuit 714, the cassette transport driving circuit 716, the white blood cell detection section 724, the focus calculating section 725 and the communication interfaces 727 and 728 so as to communicate therewith. When the control section 726 executes a control program stored in the memory, the above-described mechanisms are controlled.

The communication interface 727 is an Ethernet (registered trade name) interface. The communication interface 727 is connected to the image processing unit 73 via a communication cable so as to perform data communication therewith. In addition, the communication interface 728 is connected to the CCD camera 723 via an A/D converter 723a and is connected to the image processing unit 73 via a communication cable. An image signal (analog signal) output from the CCD camera 723 is A/D converted by the A/D converter 723a and image data (digital data) output from the A/D converter 723a is provided to the communication interface 728 to be transmitted to the image processing unit 73.

Moreover, the microscope unit 71 includes a two-dimensional bar-code reader 729. A two-dimensional bar-code indicating a specimen ID is printed on a frost section of the slide glass 7a and the two-dimensional bar-code of the slide glass 7a introduced into the microscope unit 71 is read by the two-dimensional bar-code reader 729. In this manner, the read specimen ID is provided to the control section 726.

<Configuration of Image Processing Unit 73>

Figure 7:
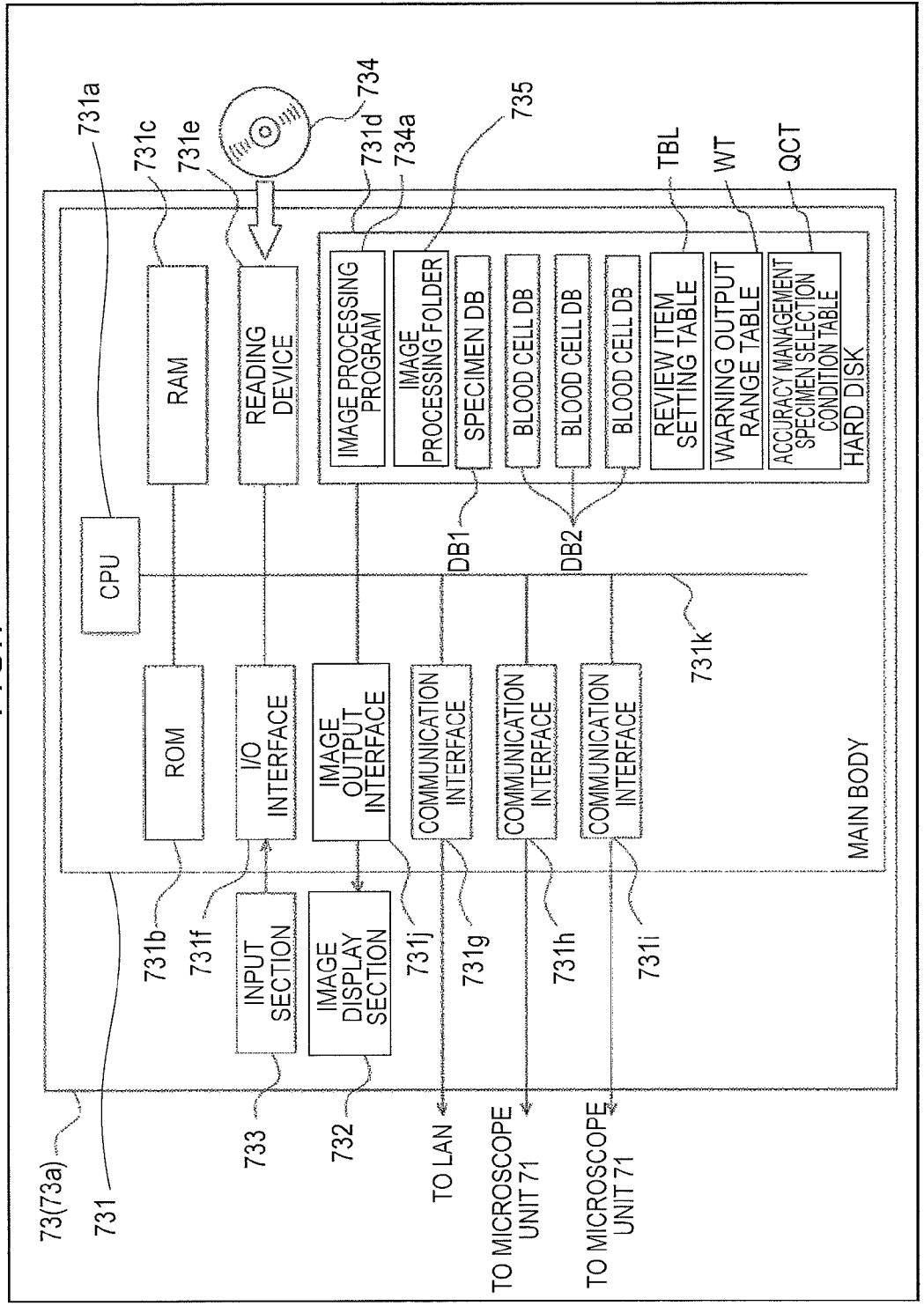
FIG. 7 is a block diagram showing the configuration of an image processing unit provided in the blood cell image display apparatus according to the embodiment.

Next, the configuration of the image processing unit 73 will be described. FIG. 7 is a block diagram showing the configuration of the image processing unit 73. The image processing unit 73 is realized by a computer 73a. As shown in FIG. 7, the computer 73a includes a main body 731, an image display section 732 and an input section 733. The main body 731 includes a CPU 731a, a ROM 731b, a RAM 731c, a hard disk 731d, a reading device 731e, an I/O interface 731f, a communication interface 731g and an image output interface 731j. The CPU 731a, the ROM 731b, the RAM 731c, the hard disk 731d, the reading device 731e, the I/O interface 731f, the communication interface 731g, a communication interface 731h, a communication interface 731i and the image output interface 731j are connected by a bus 731k.

The CPU 731a can execute a computer program loaded to the RAM 731c. The CPU 731a executes an image processing program 734a to be described later, so that the computer 73a functions as the image processing unit 73.

The ROM 731b is composed of a mask ROM, a PROM, an EPROM, an EEPROM or the like, and the computer program which is executed by the CPU 731a, data used for the computer program and the like are recorded therein.

The RAM 731c is composed of a SRAM, a DRAM or the like. The RAM 731c is used to read the image processing program 734a recorded in the hard disk 731d. Moreover, the RAM is used as an operating area of the CPU 731a when the CPU 731a executes a computer program.

In the hard disk 731d, various computer programs for execution by the CPU 731a, such as an operating system and an application program, and data which are used to execute the computer programs are installed. The image processing program 734a to be described later is also installed in the hard disk 731d.

The hard disk 731d is provided with a blood cell image folder 735 for storing blood cell images. In the blood cell image folder 735, a folder is provided for each specimen and blood cell images obtained as described later are stored in the folder. The folder provided for each specimen has a folder name including a specimen ID, and the corresponding folder can be specified by the specimen ID. The blood cell image folder 735 is set up so as to share data with the blood cell image display unit 75 and the blood cell image display unit 75 can access files stored in the blood cell image folder 735.

Figure 8B:
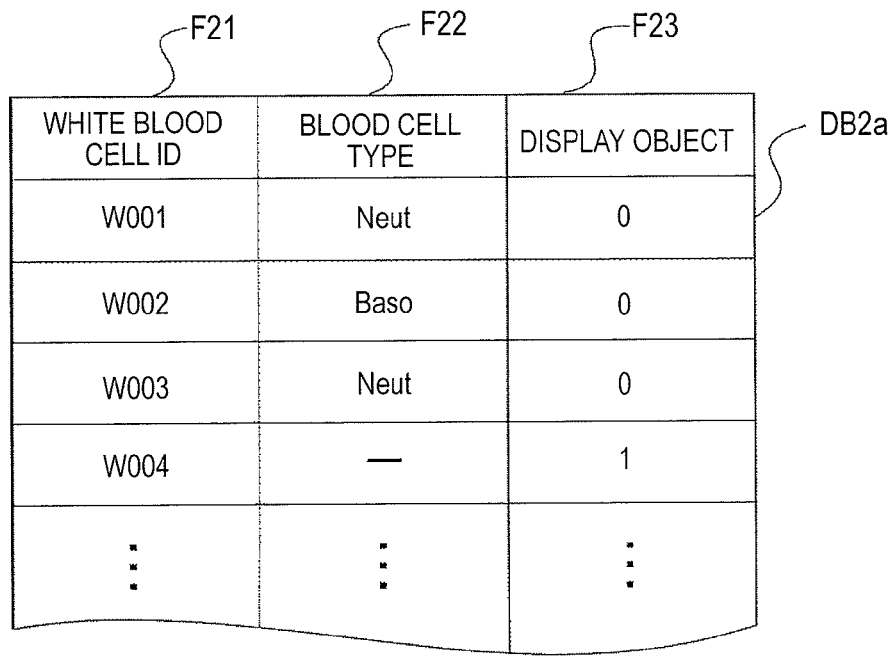
FIG. 8B is a schematic diagram showing the configuration of a blood cell database DB2.
Figure 8B:
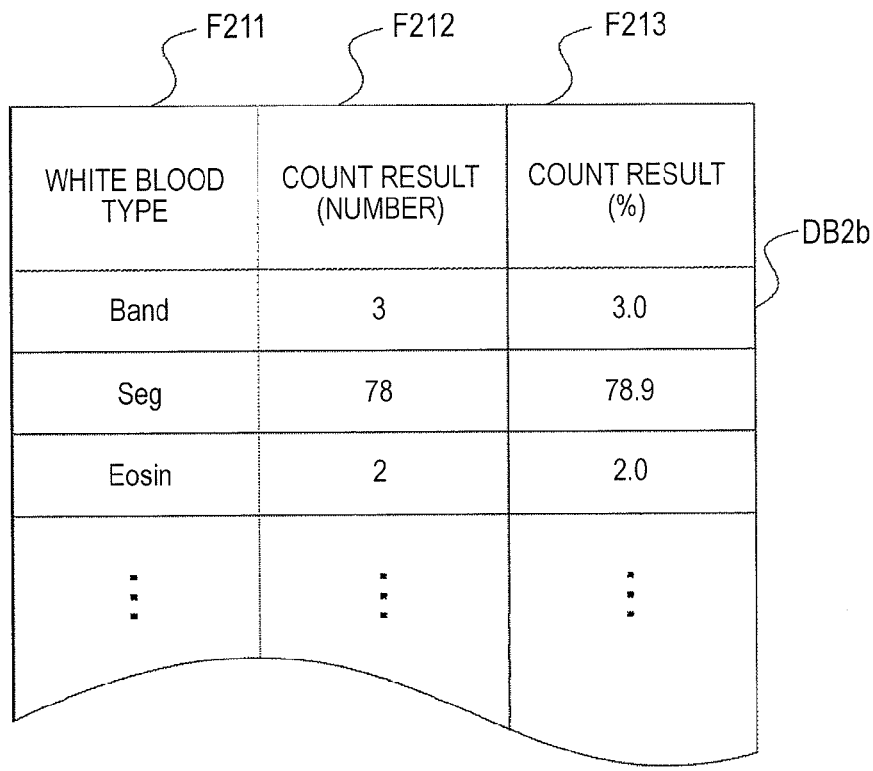

Further, the hard disk 731d is provided with a specimen database DB1 for storing information relating to specimens, and a blood cell database DB2 for storing results of the classification of white blood cells by image processing. FIG. 8A is a schematic diagram showing the configuration of the specimen database DB1 and FIG. 8B is a schematic diagram showing the configuration of the blood cell database DB2. The specimen database DB1 includes a specimen field F11 for storing specimen IDs, count result fields F111, F112, F113, . . . for storing respectively the count result for each type of the blood cell by the blood cell counting apparatus 5, fields F12, F13, F14, . . . for storing various information on results that are determined to be abnormal, such as information (white blood cell scattergram abnormality flag) showing whether a white blood cell scattergram abnormality is confirmed, information (NRBC scattergram abnormality flag) showing whether an NRBC (nucleated red blood cell) scattergram abnormality is confirmed and information (neutropenia abnormality flag) showing whether a neutropenia abnormality is confirmed. The specimen database DB1 also includes a field F15 for storing dates of measurements performed by the blood cell image counting apparatus 5. In the fields storing the information showing abnormalities, such as the white blood cell scattergram abnormality field F12, the NRBC scattergram abnormality field F13, and the neutropenia abnormality field F14, "0" is stored when an abnormality has not occurred, and "1" is stored when an abnormality has occurred. Although omitted for the simplicity of the drawing, the specimen database DB1 is provided with a field for storing patients' names, a field for storing information specifying a hospital ward, a field for storing ages of the patients, a field for storing a number N of white blood cells counted, and the like.

The blood cell database DB2 is provided for each specimen and each blood cell database DB2 includes data indicating a specimen ID. By this, the blood cell database DB2 corresponding to the specimen ID can be specified. In addition, the blood cell database DB2 is provided with a blood cell database DB2a and a blood cell database DB2b each corresponding to the specimen ID. The blood cell database DB2a is provided with a white blood cell ID field F21 for storing white blood cell IDs specifying the white blood cells, a type field F22 for storing classification results of the white blood cells, and a display object field F23 indicating whether or not the corresponding blood cell image is a display object image. In the display object field F23, "0" is stored when the corresponding blood cell image is not a display object, and "1" is stored when the corresponding blood cell image is a display object. In addition, the blood cell database DB2b is provided with a blood cell type field F211 for specifying the blood cell type, a count result (number) field F212 indicating the count number relating to each blood cell type, and a count result (%) field F213 indicating a ratio of each blood cell type to the total number of the white blood cells. The appearance number of each blood cell type in the type field F22 of the blood cell database DB2a is input in the count result (number) field F212. In addition, a ratio of a count number input to the count result (number) field F212 to the white blood cell count number N to be described later is input to the count result (%) field F213. Here, when there are unclassified white blood cells which are not classified into any blood cell type, the number of the unclassified white blood cells is subtracted from the white blood cell count number N.

In addition, in the hard disk 731d, a review item setting table TBL for setting a blood cell type which becomes a display object when a blood cell image of a specimen is displayed by the blood cell image display unit 75 is provided. FIG. 9 is a diagram schematically showing the data structure of the review item setting table TBL. The review item setting table TBL is provided with a field F31 for storing the blood cell type information which indicates the type of the blood cell, and a field F32 for storing information which indicates whether or not the blood cell image for the blood cell type is displayed.

In addition, the hard disk 731d is provided with a warning output range table WT for storing value range data which is used to determine whether or not a warning is output in a warning output process to be described later.

In addition, the hard disk 731d is provided with a selection condition table QCT for storing selection conditions for selecting the specimen which is used to calculate variation in an accuracy management to be described later.

The reading device 731e is composed of a flexible disk drive, a CD-ROM drive, a DVD-ROM drive or the like and can read the computer program or data recorded in a portable recording medium 734. In the portable recording medium 734, the image processing program 734a is stored which prompts the computer to function as the image processing unit 73. The computer 73a can read the image processing program 734a from the portable recording medium 734 and install the image processing program 734a in the hard disk 731d.

The image processing program 734a is not only provided by the portable recording medium 734 but can be also provided from an external device, which is connected to the computer 73a by an electric communication line (which may be wired or wireless) to communicate therewith via the electric communication line. For example, the image processing program 734a is stored in the hard disk of a server computer on the internet and the computer 73a accesses the server computer to download the computer program and install the computer program in the hard disk 731d.

Furthermore, in the hard disk 731d, for example, a multitasking operating system is installed such as Windows (registered trade name) which is made and distributed by Microsoft Corporation in America. In the following description, the image processing program 734a according to this embodiment operates on the above operating system.

The I/O interface 731f is composed of, for example, a serial interface such as USB, IEEE1394 or RS-232C, a parallel interface such as SCSI, IDE or IEEE1284, and an analog interface including a D/A converter and an A/D converter. The input section 733 is composed of a keyboard and a mouse and is connected to the I/O interface 731f, and the user uses the input section 733 to input data to the computer 73a.

The communication interfaces 731g and 731h are Ethernet (registered trade name) interfaces. The communication interface 731g is connected to the blood cell image display unit 75 via a LAN. In addition, the communication interface 731g is connected to the host computer 9 via the LAN so as to communicate therewith. By using the communication interface 731g, the computer 73a can send and receive data between the blood cell image display unit 75 connected to the LAN and the host computer 9 by using a predetermined communication protocol. The communication interface 731h is connected to the communication interface 727 of the microscope unit 71 via a communication cable so as to perform data communication therewith.

The communication interface 731i is connected to the communication interface 728 of the microscope unit 71 via a communication cable to perform data communication therewith. Accordingly, images captured by the CCD camera 723 are received by the communication interface 731i.

The image output interface 731j is connected to the image display section 732 composed of an LCD or a CRT to output a picture signal corresponding to the image data provided from the CPU 731a to the image display section 732. The image display section 732 displays an image (screen) in accordance with an input picture signal.

<Configuration of Blood Cell Image Display Unit 75>

The blood cell image display unit 75 is configured from a computer. The blood cell image display unit 75 is connected to the image processing unit 73 via a LAN to read and display blood cell images in the blood cell image folder 735 provided in the hard disk 731d of the image processing unit 73.

Figure 10:
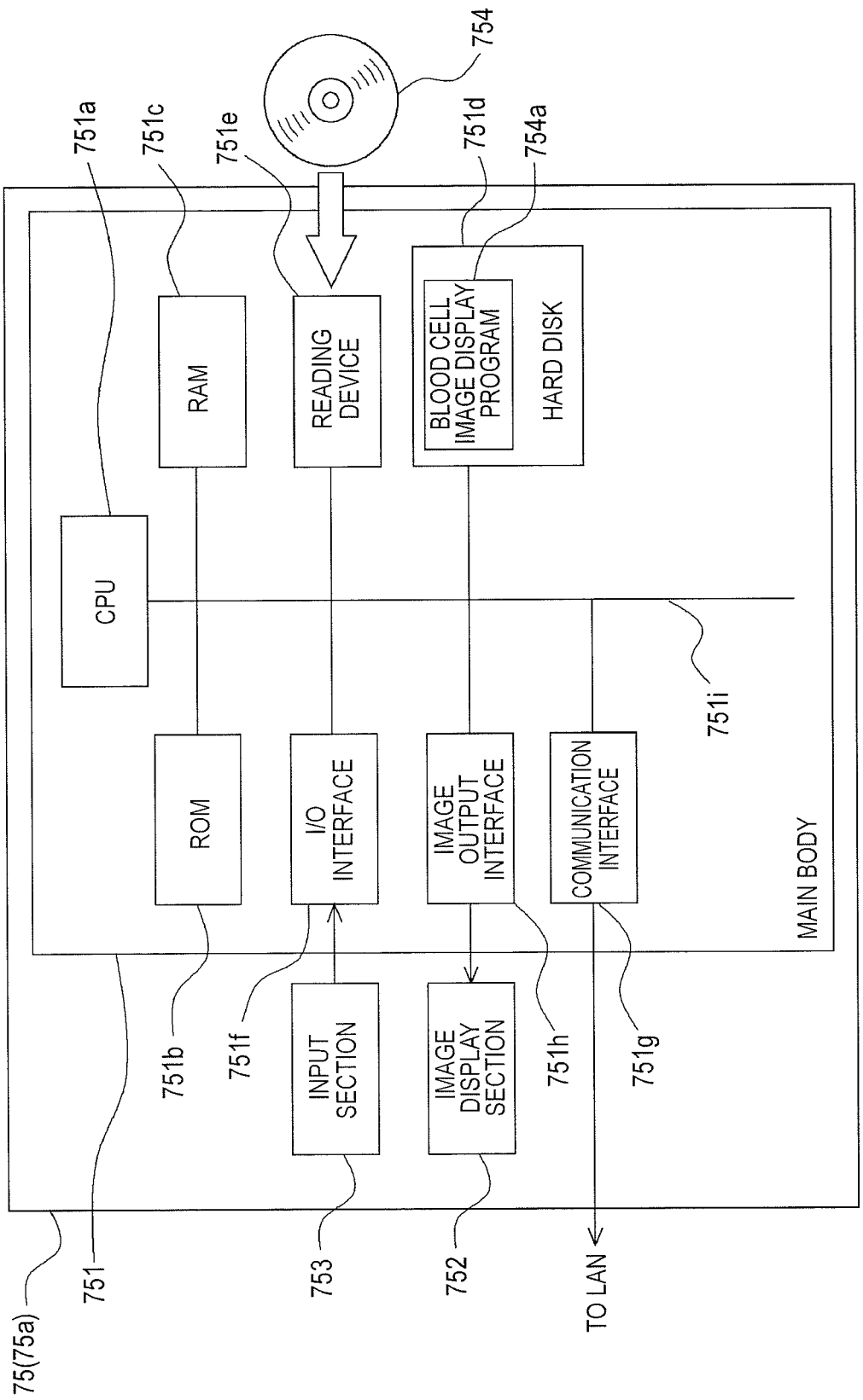
FIG. 10 is a block diagram showing the configuration of a blood cell image display unit provided in the blood cell image display apparatus according to the embodiment.

FIG. 10 is a block diagram showing the configuration of the blood cell image display unit 75. The blood cell image display unit 75 is realized by a computer 75a. As shown in FIG. 10, the computer 75a includes a main body 751, an image display section 752 and an input section 753. The main body 751 includes a CPU 751a, a ROM 751b, a RAM 751c, a hard disk 751d, a reading device 751e, an I/O interface 751f, a communication interface 751g and an image output interface 751h. The CPU 751a, the ROM 751b, the RAM 751c, the hard disk 751d, the reading device 751e, the I/O interface 751f, the communication interface 751g, and the image output interface 751h are connected by a bus 751i.

In the hard disk 751d, various computer programs for execution by the CPU 751a, such as an operating system and an application program, and data which are used to execute the computer programs are installed. A blood cell image display program 754a to be described later is also installed in the hard disk 751d.

The reading device 751e is composed of a flexible disk drive, a CD-ROM drive, a DVD-ROM drive or the like and can read the computer program or data recorded in a portable recording medium 754. In the portable recording medium 754, the blood cell image display program 754a is stored which prompts the computer to function as the blood cell image display unit 75. The computer 75a can read the blood cell image display program 754a from the portable recording medium 754 and install the blood cell image display program 754a in the hard disk 751d.

The I/O interface 751f is composed of, for example, a serial interface such as USB, IEEE1394, SAS, SATA or RS-232C, a parallel interface such as SCSI, IDE or IEEE1284, and an analog interface including a D/A converter and an A/D converter. The input section 753 composed of a keyboard and a mouse is connected to the I/O interface 751f and the user uses the input section 753 to input data to the computer 75a.

The communication interface 751g is an Ethernet (registered trade name) interface. The communication interface 751g is connected to the image processing unit 73 via a LAN. Via the communication interface 751g, the computer 75a can send and receive data between the image processing unit 73 connected to the LAN and a host computer 9 by using a predetermined communication protocol.

Since the other configurations of the blood cell image display unit 75 are the same as the configurations of the above-described image processing unit 73, description thereof will be omitted.

<Configuration of System Control Apparatus 8>

The system control apparatus 8 is composed of a computer and controls the entire specimen analyzing system 1. The system control apparatus 8 receives a specimen ID and a rack ID from the specimen loading apparatus 2 so as to obtain a measuring order from the host computer 9 using the specimen ID as a key. Moreover, the system control apparatus 8 transmits the measuring order to the specimen transport apparatus 3.

The system control apparatus 8 is realized by a computer 8a. As shown in FIG. 3, the computer 8a includes a main body 81, an image display section 82 and an input section 83. The main body 81 includes a CPU 81a, a ROM 81b, a RAM 81c, a hard disk 81d, a reading device 81e, an I/O interface 81f, a communication interface 81g and an image output interface 81h. The CPU 81a, ROM 81b, RAM 81c, hard disk 81d, reading device 81e, I/O interface 81f, communication interface 81g and image output interface 81h are connected to each other by a bus 81j.

In the hard disk 81d, various computer programs for execution by the CPU 81a, such as an operating system and an application program, and data which are used to execute the computer programs are installed. A system control program 84a to be described later is also installed in the hard disk 81d.

The reading device 81e is composed of a flexible disk drive, a CD-ROM drive, a DVD-ROM drive or the like and can read the computer program or data recorded in a portable recording medium 84. In the portable recording medium 84, the system control program 84a for prompting the computer to function as the system control apparatus 8 is stored. The computer 8a can read the system control program 84a from the portable recording medium 84 to install the system control program 84a in the hard disk 81d.

The I/O interface 81f is composed of, for example, a serial interface such as USB, IEEE1394 or RS-232C, a parallel interface such as SCSI, IDE or IEEE1284, and an analog interface including a D/A converter and an A/D converter. The input section 83 composed of a keyboard and a mouse is connected to the I/O interface 81f and the user uses the input section 83 to input data to the computer 52a.

The communication interface 81g is an Ethernet (registered trade name) interface. The communication interface 81g is connected to the specimen loading apparatus 2, the specimen transport apparatus 3, the specimen accommodating apparatus 4 and the host computer 9 via a LAN. Via the communication interface 81g, the computer 8a can send and receive data to and from the above respective apparatuses connected to the LAN by using a predetermined communication protocol.

Since the other configurations of the system control apparatus 8 are the same as the configurations of the above-described information processing unit 52, description thereof will be omitted.

<Configuration of Host Computer 9>

The host computer 9 is composed of a computer and includes a CPU, a ROM, a RAM, a hard disk, a communication interface and the like. The communication interface is connected to the above-described LAN so as to communicate with the system control apparatus 8, the information processing unit 52 of the blood cell counting apparatus 5, the image processing unit 73 of the blood cell image classifying apparatus 7, the specimen loading apparatus 2, the specimen transport apparatus 3 and the specimen accommodating apparatus 4. In the hard disk, measuring orders are stored. When request data for a measuring order including a specimen ID is received from another apparatus, measuring data corresponding to the specimen ID is read from the hard disk and transmitted to the apparatus as a request source. Since the other configurations of the host computer 9 are the same as the configurations of the above-described other computers, description thereof will be omitted.

Hereinafter, an operation of the specimen analyzing system 1 according to this embodiment will be described.

<Operation of Specimen Loading Apparatus 2>

The user places a sample rack accommodating a specimen container in the specimen delivery unit 21a and operates an operating panel (not shown) of the specimen delivery unit 21a to issue an analysis start instruction to the specimen analyzing system 1. A control section of the specimen delivery unit 21a receives the analysis start instruction and starts the movement of the sample rack in accordance with the instruction. The sample rack placed in the specimen delivery unit 21a is moved backward on the specimen delivery unit 21a and is then moved to the left. The sample rack is transferred to the bar-code reading unit 22.

The sample rack introduced into the bar-code reading unit 22 is moved to the left at single pitch intervals on the transport path by a control section of the bar-code reading unit 22. A rack bar-code of the sample rack and a specimen bar-code of the specimen container are read by the bar-code reader and a rack ID and a specimen ID are transmitted to the system control apparatus 8. Next, the sample rack is moved to the left to be delivered to the specimen delivery unit 21b. A control section of the specimen delivery unit 21b moves the received sample rack. The sample rack is moved on the specimen delivery unit 21b and is then moved to the left. The sample rack is transferred to the rack slider 32.

<Measuring Order Obtaining Operation of System Control Apparatus 8>

Next, an operation of the system control apparatus 8 will be described. The system control apparatus obtains a measuring order of a specimen (blood specimen) by the specimen ID received from the specimen loading apparatus 2. Herein, the measuring order is data indicating an instruction of an analysis item to be analyzed for the blood specimen, and includes attribute information of the specimen, such as the specimen ID, patient ID and name of the patient, and information of the analysis item.

Figure 11A:
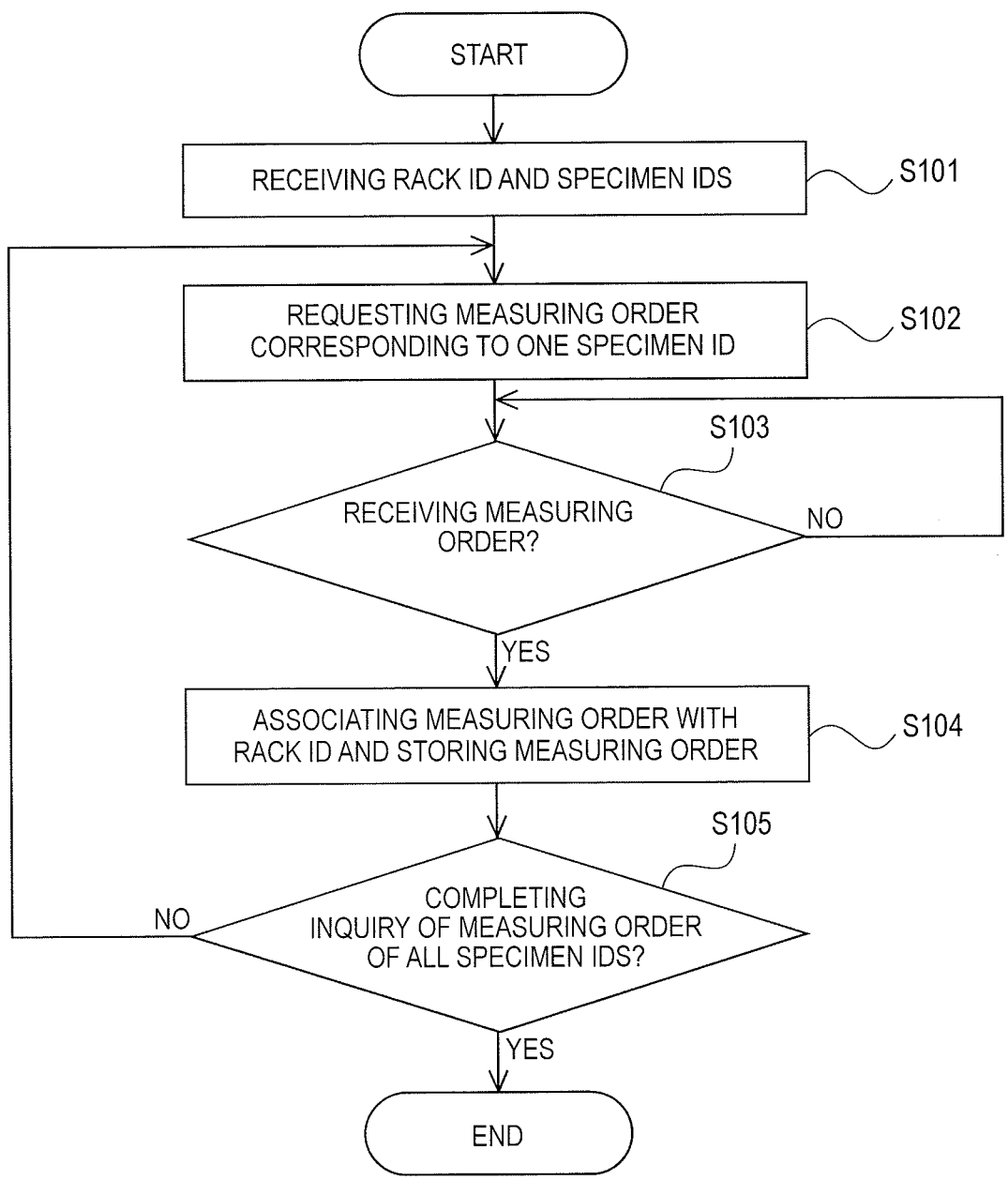
FIG. 11A is a flowchart showing the procedure of a measuring order obtaining process of a system control apparatus according to the embodiment.

FIG. 11A is a flowchart showing the procedure of a process of obtaining a measuring order. A rack ID and specimen IDs transmitted from the specimen loading apparatus 2 are received by the communication interface 81g of the system control apparatus 8 (Step S101). The system control program 84a which is executed by the CPU 81a of the system control apparatus 8 is an event-driven program, and in the CPU 81a, a process of Step S102 is invoked when an event occurs in which the rack ID and the specimen IDs are received.

In Step S102, the CPU 81a transmits one of the received specimen IDs and requests a measuring order corresponding to the specimen ID from the host computer 9 (Step S102). The CPU 81a stands by to receive the measuring order (No in Step S103). When the system control apparatus 8 receives the measuring order transmitted from the host computer 9 (Yes in Step S103), the CPU associates the received measuring order with the rack ID and stores the measuring order in the hard disk 81d (Step S104). The CPU 81a determines whether the specimen IDs corresponding to the rack ID, that is, all the specimen IDs of all the specimen containers accommodated in the sample rack having the rack ID have been subjected to a measuring order inquiry (Step S105). When a specimen ID not subjected to a measuring order inquiry exists (No in Step S105), the CPU returns the process to Step S102 and requests a measuring order corresponding to the specimen ID not yet subjected to the measuring order inquiry from the host computer 9.

On the other hand, when all of the specimen IDs have been subjected to the measuring order inquiry (Yes in Step S105), the CPU 81a completes the process.

<Measuring Order Transmitting Operation of System Control Apparatus 8>

As described later, the specimen transport apparatus 3 transmits a rack ID to the system control apparatus 8 to request a measuring order corresponding to the rack ID. The system control apparatus 8 transmits the measuring order to the specimen transport apparatus 3 in accordance with the request.

Figure 11B:
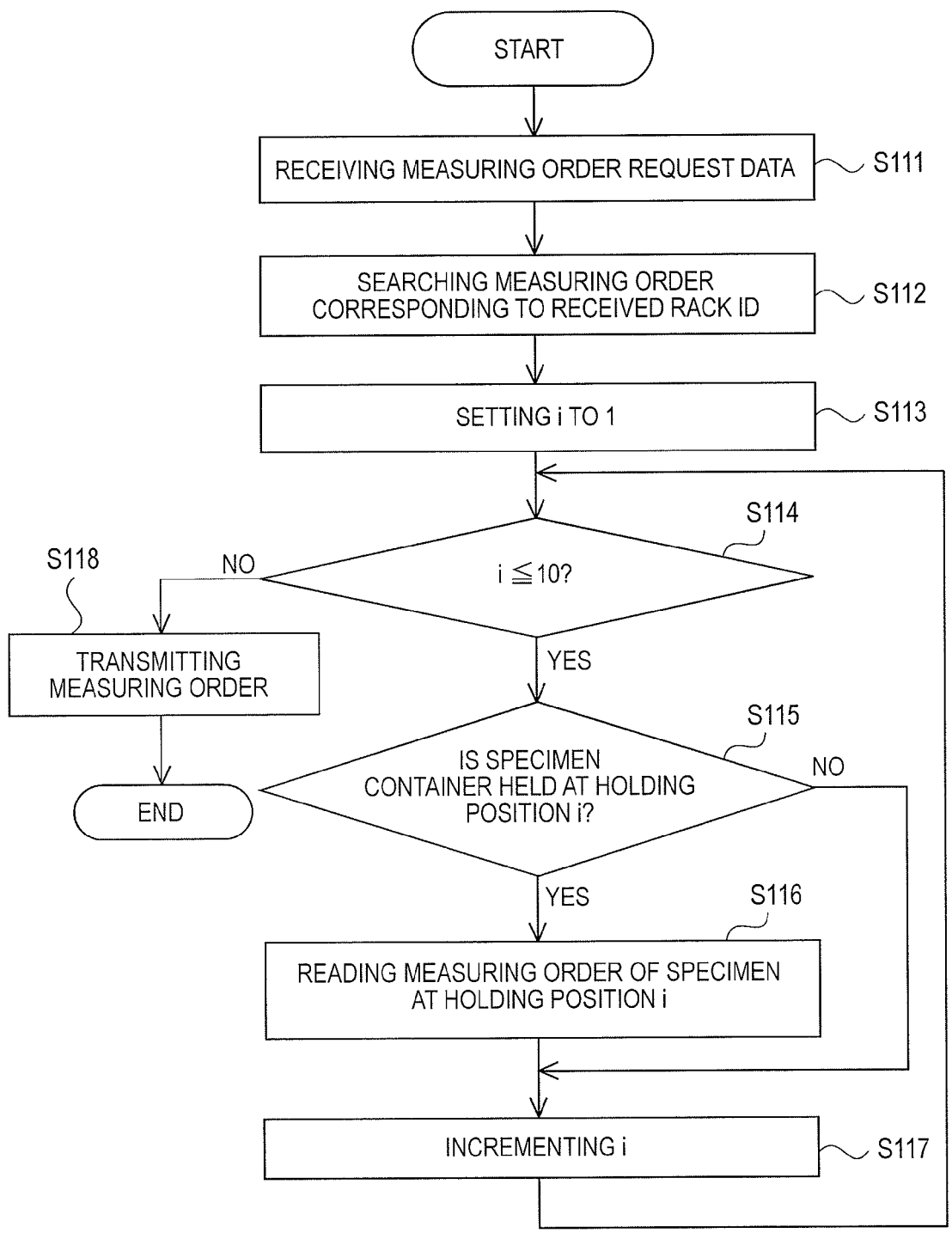
FIG. 11B is a flowchart showing the procedure of a measuring order transmitting process of the system control apparatus according to the embodiment.

FIG. 11B is a flowchart showing the procedure of a measuring order transmitting process. Request data for a measuring order including the rack ID transmitted from the specimen transport apparatus 3 is received by the communication interface 81g of the system control apparatus 8 (Step S111). In the CPU 81a, a process of Step S112 is invoked when an event occurs in which the request data of the measuring order is received.

In Step S112, the CPU 81a searches for the measuring order corresponding to the received rack ID from the hard disk 81d. Next, the CPU 81a sets a variable i indicating the holding position of the sample rack to 1 (Step S113) and determines whether i is equal to or less than 10 (Step S114). When i is equal to or less than 10 (Yes in Step S114), the CPU 81a determines whether the specimen container is held at a holding position i (whether there is the measuring order corresponding to the holding position i) (Step S115). When the specimen container is not held at the holding position i (No in Step S115), the CPU 81a performs a process of Step S117.

When the specimen container is held at the holding position i (Yes in Step S115), the CPU 81a reads the measuring order of the blood specimen at the holding position i from the hard disk 81d (Step S116). Then, in Step S117, the CPU 81a increments i by 1 and returns the process to Step S114. In Step S114, when i is not equal to or less than 10 (No in Step S114), the CPU 81a transmits the measuring order stored in the RAM 81c to the specimen transport apparatus 3 as a measuring order request source (Step S118) and completes the process.

<Operation of Specimen Transport Apparatus 3>

Herein, an operation of the specimen transport apparatus 3 disposed in front of the blood cell counting apparatus 5 will be described. When a sample rack is transported to the rack slider 32 from the upstream side of transport, a sensor (not shown) detects the arrival of the sample rack. When the arrival of the sample rack is detected, a rack ID is read by the bar-code reader (not shown) from the rack bar-code of the sample rack. The control section of the specimen transport apparatus 3 transmits measuring order request data including the rack ID to the system control apparatus 8. In this manner, a measuring order is transmitted from the system control apparatus 8 as described above and the specimen transport apparatus 3 receives the measuring order. A specimen bar-code reader (not shown) is provided on the measuring line 31a of the specimen transport apparatus 3 to sequentially read specimen bar-codes of the specimen containers accommodated in the sample rack. The control section of the specimen transport apparatus 3 transmits aspiration instruction data including the measuring order corresponding to the read specimen ID to the blood cell counting apparatus 5.

After the aspiration of a specimen by the blood cell counting apparatus 5, an aspiration completion notification signal is transmitted from the blood cell counting apparatus 5. When the specimen transport apparatus 3 receives the aspiration completion notification signal from the blood cell counting apparatus 5, the sample rack is moved by one specimen distance to read the specimen ID of the next specimen container and repeatedly performs the above-described operation. The sample rack in which the aspiration of all the specimens has been completed is transported to the downstream side by the specimen transport apparatus 3.

<Operation of Blood Cell Counting Apparatus 5>

Figure 12:
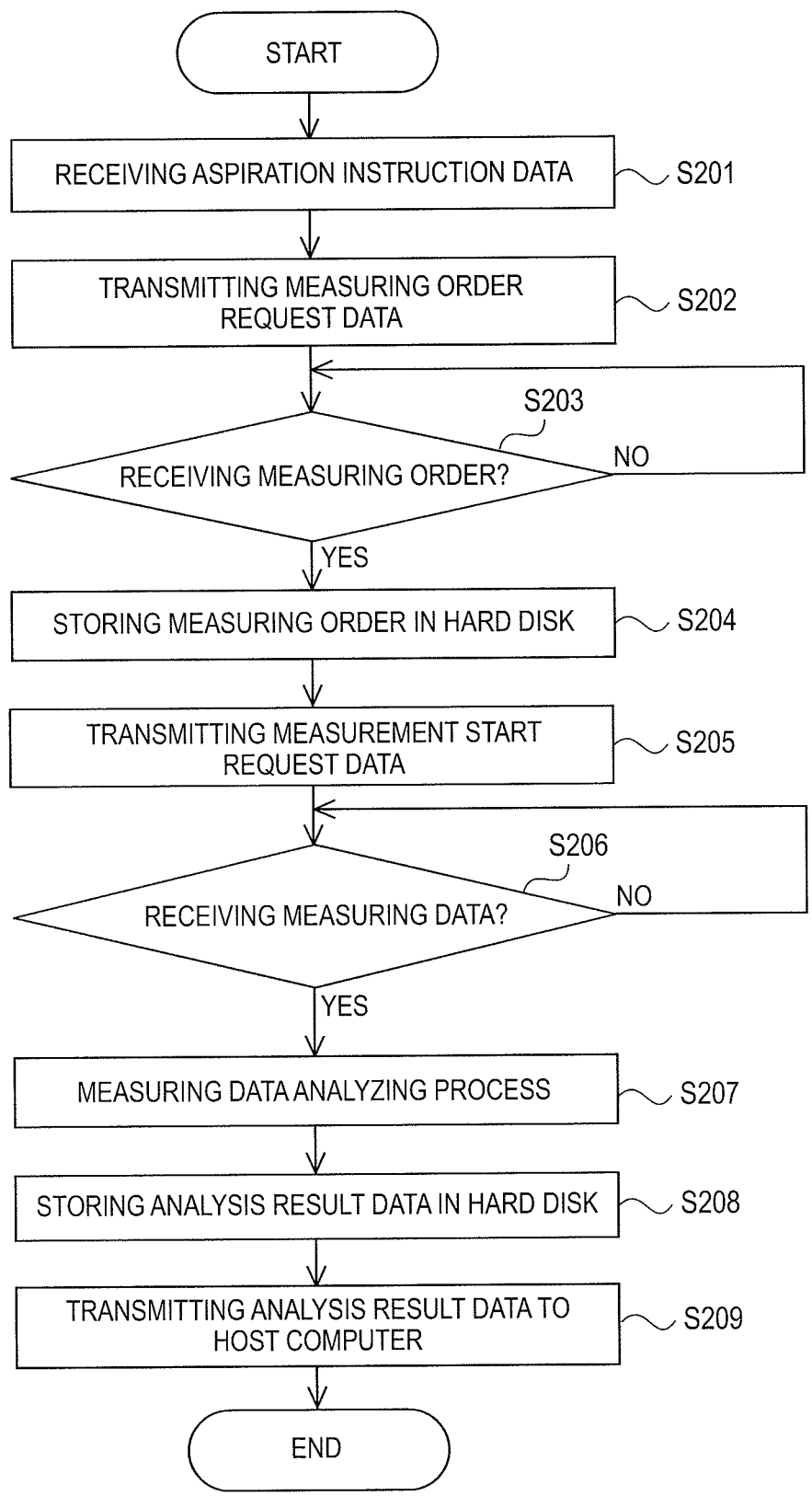
FIG. 12 is a flowchart showing the flow of an operation of the information processing unit of the blood cell counting apparatus according to the embodiment.

Next, an operation of the blood cell counting apparatus 5 will be described. FIG. 12 is a flowchart showing the flow of an operation of the information processing unit 52 of the blood cell counting apparatus 5. Aspiration instruction data transmitted from the specimen transport apparatus 3 is received by the communication interface 521g of the information processing unit 52 via the control section 515 of the measuring unit 51 (Step S201). The analysis program 524a which is executed by the CPU 521a of the information processing unit 52 is an event-driven program, and in the CPU 521a, a process of Step S202 is invoked when an event occurs in which the aspiration instruction data is received.

In Step S202, the CPU 521a transmits order request data including the specimen ID included in the aspiration instruction data to the host computer 9 via the communication interface 521g (Step S202) to inquire about a measuring order. Then, the CPU 521a stands by to receive the measuring order (No in Step S203). When the measuring order transmitted from the host computer 9 is received by the communication interface 521g of the information processing unit 52 (Yes in Step S203), the CPU stores the received measuring order in the hard disk 521d (Step S204).

Next, the CPU 521a transmits measurement start request data including the analysis item included in the stored measuring order to the measuring unit 51 (Step S205). The control section 515 of the measuring unit 51 receives the measurement start request data, and thus the blood specimen is measured with respect to the analysis item included in the measurement start request data. After the measurement, the control section 515 of the measuring unit 51 transmits the measuring data (raw data) reflecting the side-scattered light intensity and the fluorescent intensity obtained by the measurement to the information processing unit 52. The CPU 521a stands by to receive the measuring data (No in Step S206). When the measuring data is received by the communication interface 521g (Yes in Step S206), the CPU performs a process to analyze the measuring data (Step S207), classifies the blood cells included in the specimen and counts the number of blood cells for each type to create a scattergram in which the classified blood cells are color-coded for each type. In the measuring data analyzing process, the count result of subclasses of the white blood cell, such as Band, Seg, Eosin, and the like, is obtained as a ratio to the total number of the white blood cells. Further, in the measuring data analyzing process, abnormalities, such as an abnormality of a white blood cell scattergram (scattergram for classifying white blood cells for each type), an abnormality of an NRBC scattergram (scattergram for detecting a nucleated red blood cell), a neutropenia abnormality indicating that the number of neutrophils falls below a predetermined normal range, a neutrophilia abnormality indicating that the number of neutrophils is more than the normal range, a monocytosis abnormality indicating that the number of monocytes is more than a predetermined normal range, an eosinophilia abnormality indicating that the number of eosinophils is more than a predetermined normal range, a basophilic leukocytosis abnormality indicating that the number of basophils is more than a predetermined normal range, a leucopenia abnormality indicating that the total number of white blood cells falls below a predetermined normal range, a leukocytosis abnormality indicating that the total number of white blood cells is more than a predetermined normal range, and an erythroblastosis abnormality indicating that the number of erythroblasts is more than a predetermined normal range, are detected, and an abnormality flag indicating that an abnormality is detected is added to the analysis result data generated by the analyzing process. The analysis result data generated by the measuring data analyzing process is stored together with the patient information or the like included in the measuring order in the hard disk 521d (Step S208) and is transmitted to the host computer 9 (Step S209). The host computer 9 integrates the analysis result data and the above-described measuring order and stores the result thereof in the hard disk. After the process of Step S209, the CPU 521a completes the process.

<Operation of Smear Preparing Apparatus 6>

After receiving the above-described analysis result data, the host computer 9 determines the specimen as an object for smear examination when the analysis result data includes a certain abnormality. In addition, the host computer determines a number N of white blood cells counted in the smear examination in accordance with the type or degree of the abnormality. For the specimen which is determined as an object for smear examination, a new measuring order of the smear examination including the patient information, the analysis result (including the detected abnormality flag) of the blood cell counting apparatus 5 and the number N is generated and stored in the hard disk of the host computer 9. After that, when the specimen measuring order is inquired by the system control apparatus 8 as described above, the measuring order of the smear examination is transmitted to the system control apparatus 8. Furthermore, in accordance with the inquiry of the specimen transport apparatus 3 which is disposed in front of the smear preparing apparatus 6 as described above, the measuring order is provided to the specimen transport apparatus 3.

In this case, the sample rack is transported on the measuring line 31a of the specimen transport apparatus 3, and the specimen which is the object for smear examination is aspirated by the smear preparing apparatus 6 by a predetermined amount. Then, the smear preparing apparatus 6 drops the specimen on a slide glass, and thinly spreads and dries the blood specimen on the slide glass. The slide glass is dipped in a stain solution and is then dried again. In this manner, a smear is prepared. The smear prepared in this manner is transported to the microscope unit 71 of the blood cell image classifying apparatus 7.

<Operation of Specimen Accommodating Apparatus 4>

The sample rack delivered from the specimen transport apparatus 3 at the furthest point on the downstream side of the transport is introduced into the specimen accommodating apparatus 4. The specimen accommodating apparatus 4 transports the sample rack on a rack placing section and accommodates the sample rack.

<Operation of Blood Cell Image Classifying Apparatus 7>

Next, an operation of the blood cell image classifying apparatus 7 according to this embodiment will be described.

<Blood Cell Image Registration Operation>

Figure 13:
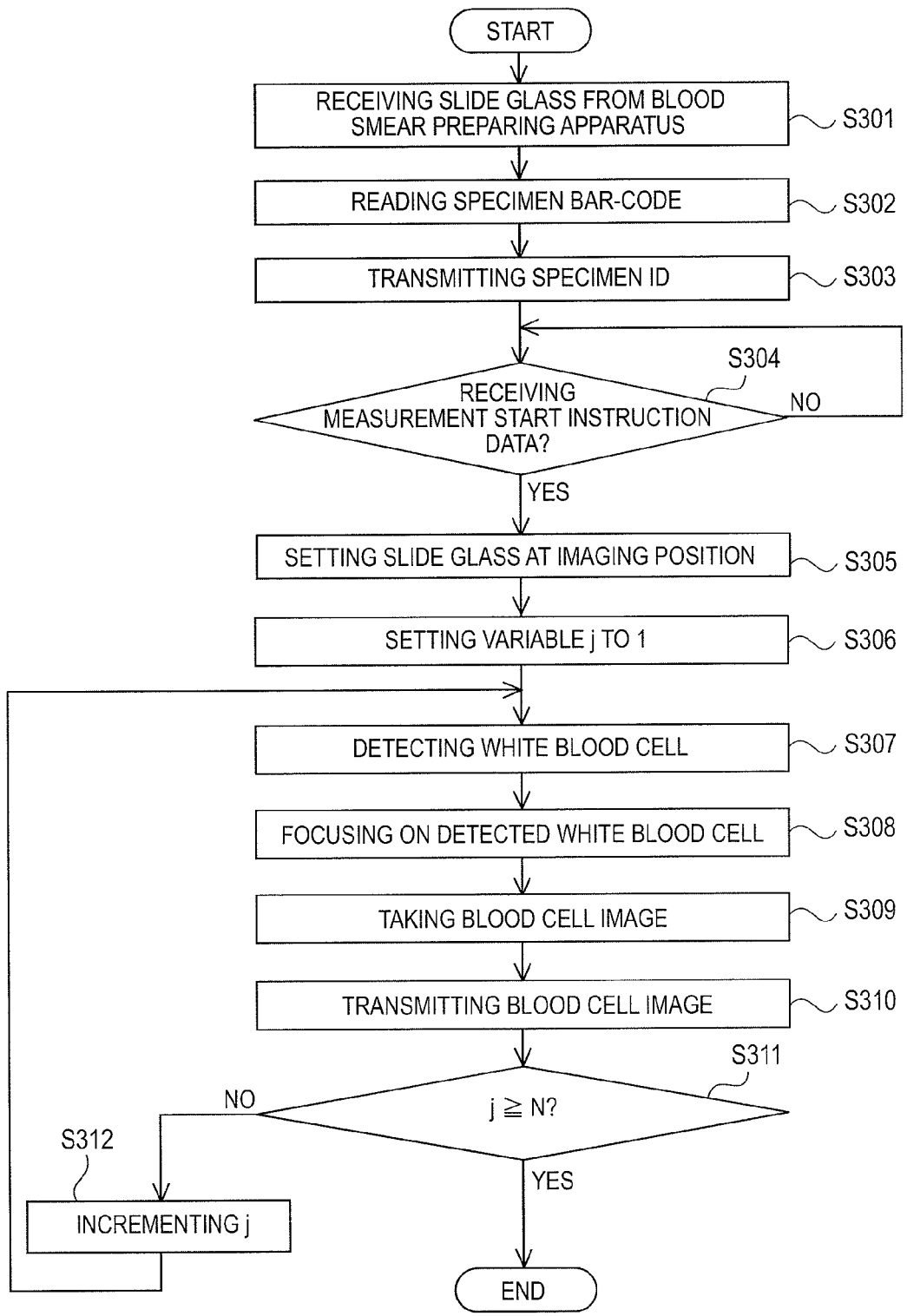
FIG. 13 is a flowchart showing the procedure of an operation of the microscope unit in a blood cell image registration operation.
Figure 14A:
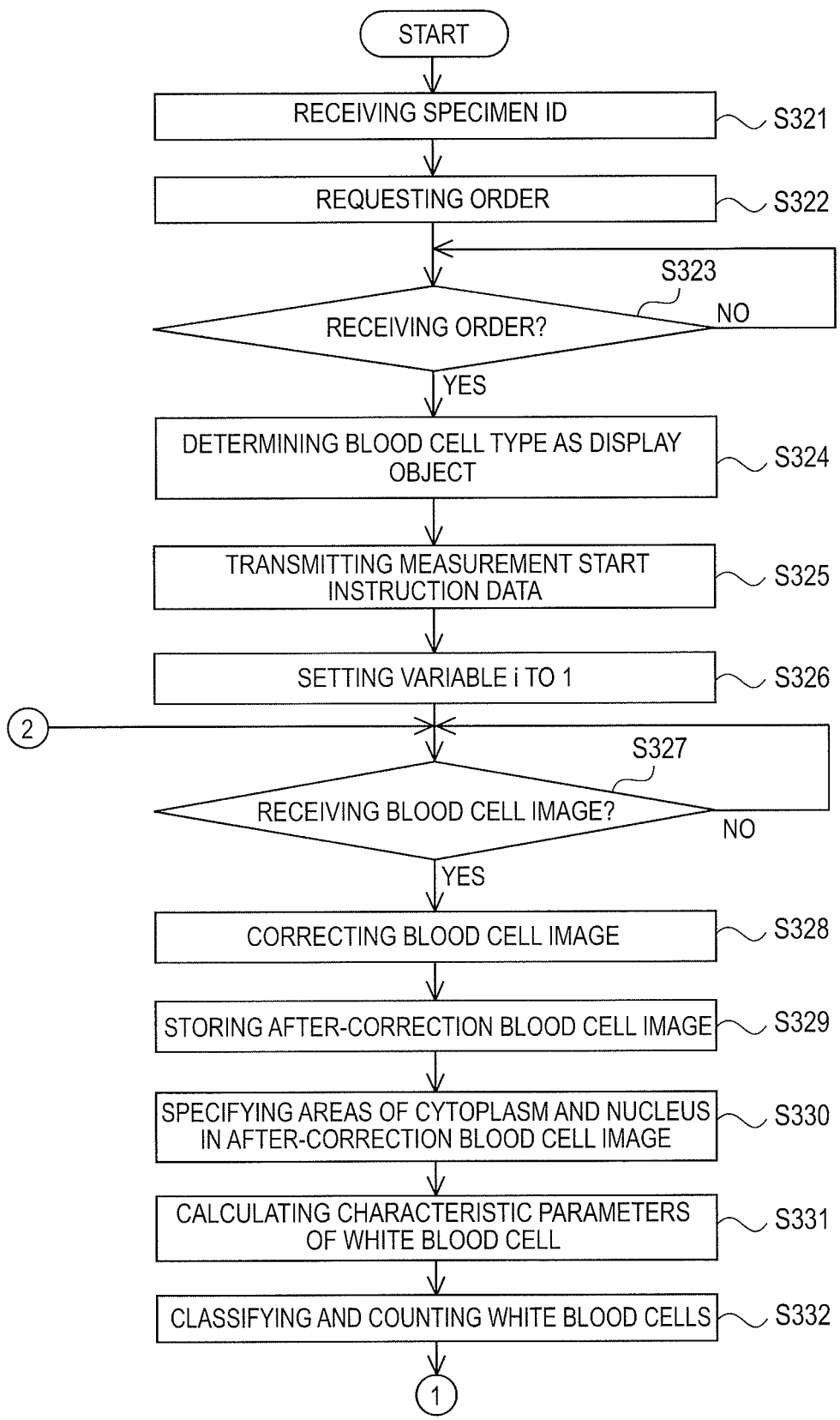
FIG. 14A is a flowchart (first half) showing the procedure of an operation of the image processing unit in the blood cell image registration operation.
Figure 14B:
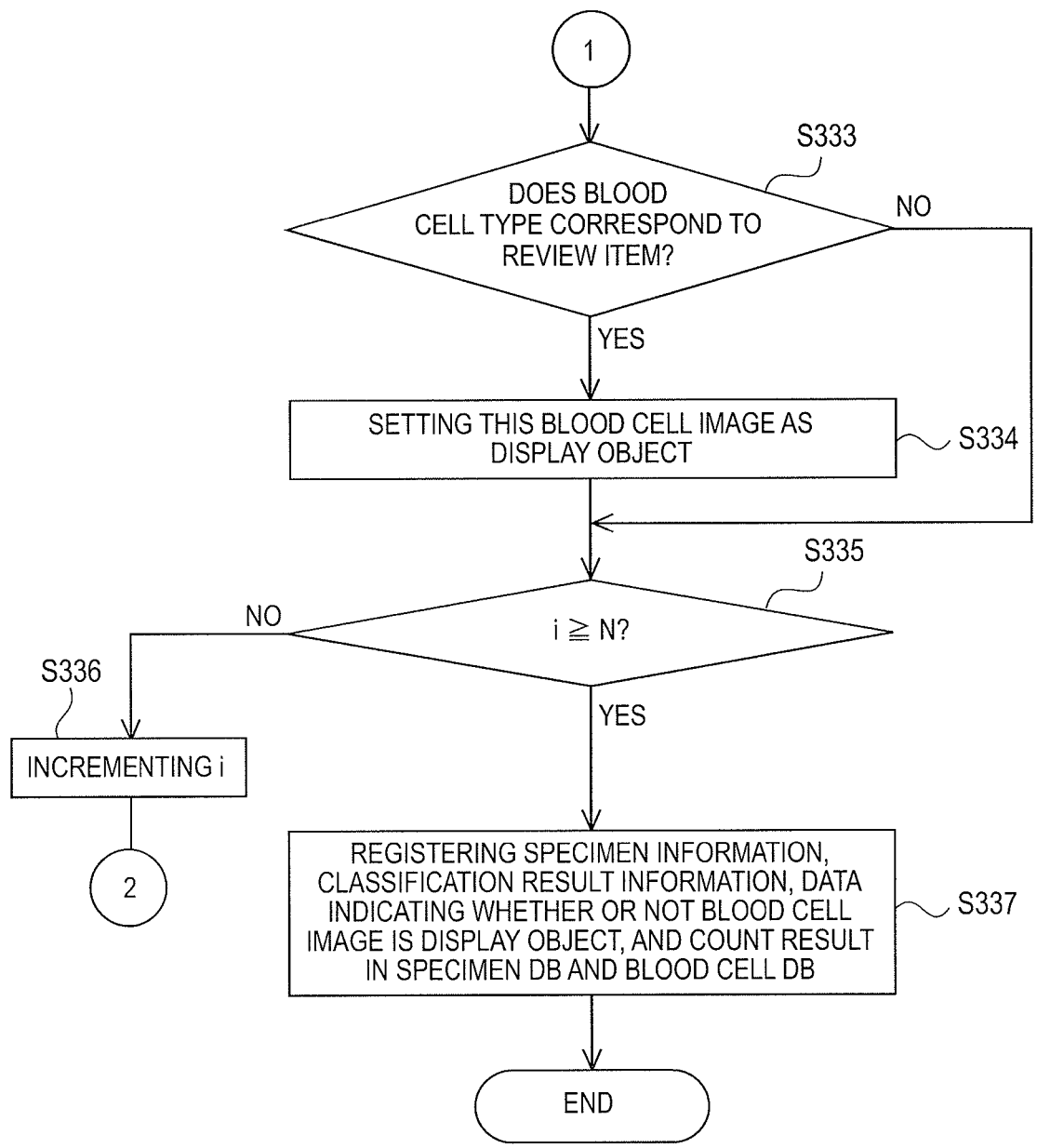
FIG. 14B is a flowchart (second half) showing the procedure of the operation of the image processing unit in the blood cell image registration operation.

First, a blood cell image registration operation of imaging blood cells using the blood cell image display apparatus 7 and storing the blood cell image will be described. FIG. 13 is a flowchart showing the procedure of an operation of the microscope unit 71 in the blood cell image registration operation, and FIGS. 14A and 14B are flowcharts showing the procedure of an operation of the image processing unit 73 in the blood cell image registration operation. When receiving the slide glass 7a from the blood smear preparing apparatus 6, the microscope unit 71 detects the slide glass via a sensor (not shown) (Step S301). A control program which is executed by the control section 726 is an event-driven program, and in the control section 726 of the microscope unit 71, a process of Step S302 is invoked when an event occurs in which the slide glass 7a is received from the blood smear preparing apparatus 6.

In Step S302, the control section 726 transports the slide cassette 715 accommodating the received slide glass 7a to a predetermined bar-code reading position and the specimen bar-code is read by the two-dimensional bar-code reader 729 (Step S302). Next, the control section 726 transmits the specimen ID obtained in Step S302 to the image processing unit 73 via the communication interface 727 (Step S303).

The specimen ID transmitted from the microscope unit 71 is received by the communication interface 731h of the image processing unit 73 (Step S321 of FIG. 14A). The image processing program 734a which is executed by the CPU 731a of the image processing unit 73 is an event-driven program, and in the CPU 731a, a process of Step S322 is invoked when an event occurs in which the specimen ID is received.

In Step S322, the CPU 731a transmits order request data including the received specimen ID to the host computer 9 via the communication interface 731g (Step S322). The order transmitted from the host computer 9 includes the specimen ID, the patient's name, the patient's sex, hospital ward information, comments, analysis results of the blood cell counting apparatus 5 (numerical data such as the number of white blood cells and the number of red blood cells (count result)), various pieces of abnormality information (white blood cell scattergram abnormality flag, NRBC scattergram abnormality flag, neutropenia abnormality flag, neutrophilia abnormality flag, monocytosis abnormality flag, eosinophilia abnormality flag, basophilic leukocytosis abnormality flag, leukopenia abnormality flag, leukocytosis abnormality flag, erythroblastosis abnormality flag, etc.) detected by the blood cell counting apparatus 5, and the data of the number N of white blood cells counted. The CPU 731a stands by to receive the order (No in Step S323). When the measuring order is received (Yes in Step S323), the CPU determines the blood cell type as a display object (Step S324) according to the review item setting table TBL, and stores data indicating the blood cell type determined as the display object (review item) in the RAM 731c.

Next, the CPU 731a transmits measurement start instruction data including the number N of white blood cells counted, which is included in the measuring order, to the microscope unit 71 by the communication interface 731h (Step S325), and sets a variable i indicating the number of blood cell images analyzed to 1 (Step S326).

Herein, the microscope unit 71 stands by to receive the measurement start instruction data (No in Step S304 of FIG. 13). When the measurement start instruction data transmitted from the image processing unit 73 is received by the communication interface 727 of the microscope unit 71 (Yes in Step S304), the control section 726 transports the slide cassette 715 to a predetermined position to hold the slide glass 7a which has been stopped at the predetermined position by the chuck section 717. Then, by retracting the chuck section 717, the slide glass is drawn from the slide cassette 715 and is set at a predetermined position (imaging position) in the XY stage 711 (Step S305). In addition, the control section 726 sets a variable j indicating the number of imaging operations to 1 (Step S306).

Figure 15:
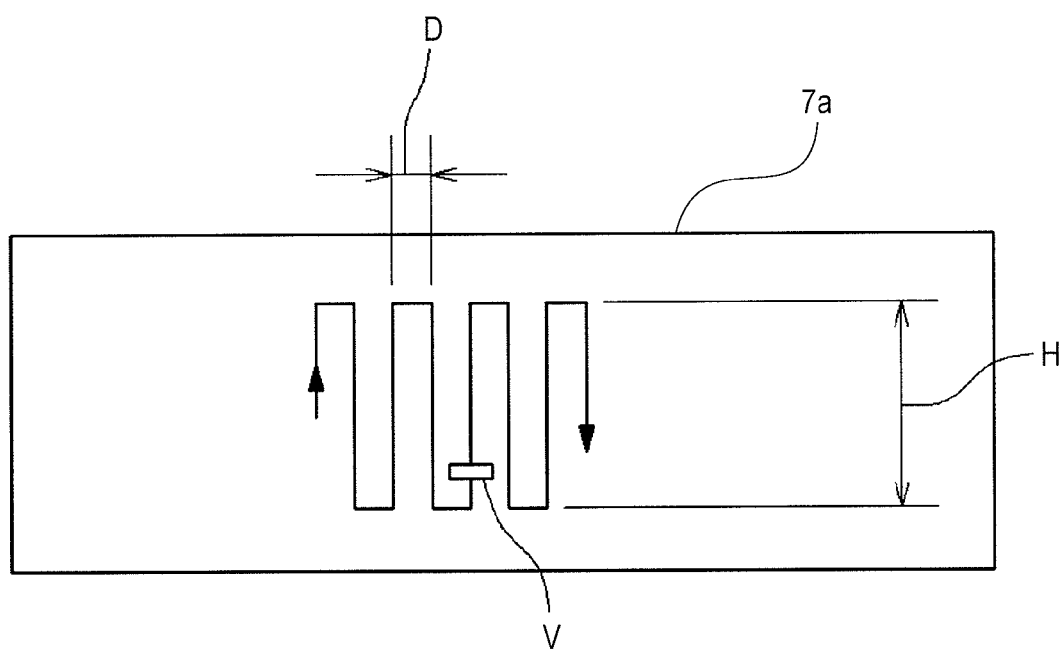
FIG. 15 is a diagram explaining a scanning pattern of a specimen on a slide glass in white blood cell detection.

Next, the white blood cells in the blood applied to the slide glass 7a are detected (Step S307). The above detection is performed using the sensor 722. The sensor 722 is a line sensor and has a field of view of about 400 µm. FIG. 15 is a diagram explaining a scanning pattern of the specimen on the slide glass in the white blood cell detection. The control section 726 moves the XY stage 711 in the X and Y directions so that the sensor 722 performs a scan operation on the slide glass 7a in a substantially zigzag manner from one end toward the other end in the longitudinal direction (see FIG. 15 for reference). Generally, an interval D in the longitudinal direction of the slide glass 7a of the substantial zigzag scanning is set in the range of about 300 to 500 µm from the viewpoint of preventing detection failures and increasing scanning efficiency. A dimension H in the width direction of the slide glass 7a being scanned is set in the range of about 14 to 18 mm because the width of the slide glass 7a is normally about 26 mm.

Figure 16A:
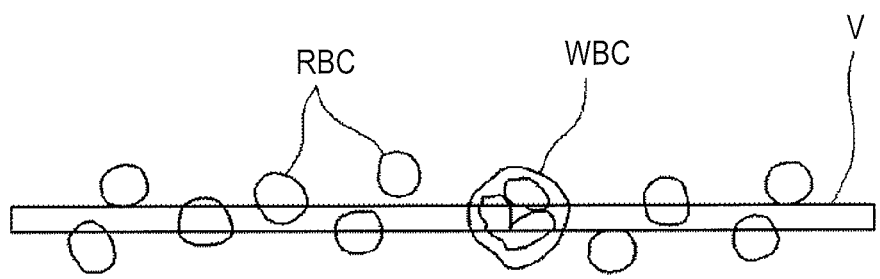
FIG. 16A is a diagram explaining the field of view of a line sensor for white blood cell detection.
Figure 16B:
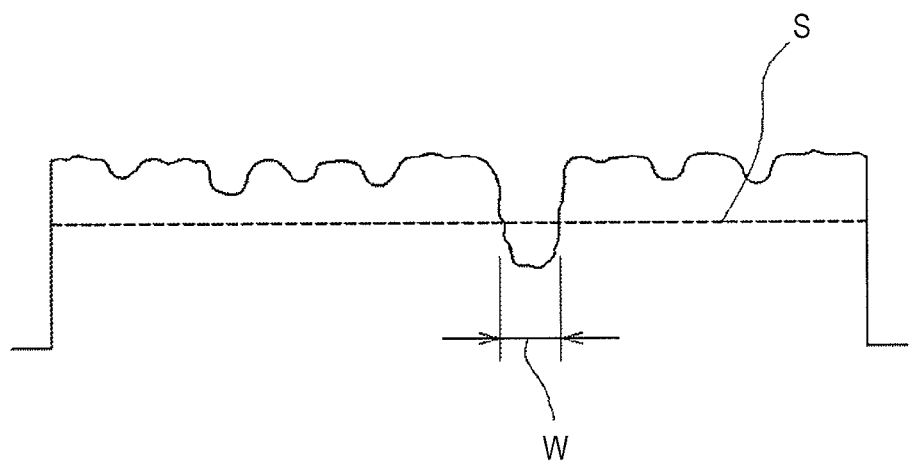
FIG. 16B is a diagram showing the signal waveform of the line sensor for white blood cell detection.

Red blood cells do not absorb much red color component of light, but the nucleus of a white blood cell does absorb a large amount of the red color component of light. Accordingly, by detecting the red color component, the white blood cells and the red blood cells can be easily distinguished. FIG. 16A is a diagram explaining the field of view of the line sensor 722, and FIG. 16B is a diagram showing a signal waveform of the line sensor 722. FIG. 16A shows that a white blood cell WBC is present in a field of view V of the line sensor 722. In this case, as shown in FIG. 16B, the red color component of a signal detected by the line sensor 722 has a value equal to or less than a reference value S in a part in which the white blood cell WBC is present. Using this phenomenon, the white blood cells can be detected in the blood. By detecting the width W of the portion in which the red color component of the signal has a value equal to or less than the reference value S, it is checked whether the portion emitting the signal is the nucleus of the white blood cell.

Next, the control section 726 performs an auto-focus operation (Step S308). As shown in FIG. 6, the direction of the light passing through the slide glass 7a and the objective lens 712 is changed by a prism mirror 719a, and the light is divided into light which is directed to the CCD camera 723 and light which is directed to the sensors 721 and 722 by the half mirrors 719. The line sensor 721 for auto-focusing is composed of two line sensors 721a and 721b.

The line sensor 721a which is one of the two line sensors 721a and 721b for auto-focusing is disposed in front of (close to the objective lens on the optical path) a focus position (a position which is in focus), and the other line sensor 721*b* is disposed behind (far from the objective lens on the optical path) the focus position. In addition, the position of the objective lens is adjusted on the basis of a value which is obtained by the integral of the difference between the output signals of the two line sensors, so that the focus of the objective lens is on the specimen on the slide glass.

Next, the control section 726 instructs the communication interface 728 to take and transmit the image of the CCD camera 723. Thus, the image of the white blood cell detected in Step S307 is taken (Step S309) and the blood cell image is transmitted to the image processing unit 73 (Step S310). After that, the control section 726 determines whether the required counted number of the white blood cells has been satisfied, that is, whether j is equal to or greater than N (Step S311). When j is less than N (No in Step S311), the control section increments j by 1 (Step S312) and returns the process to Step S307 to repeat the detection of the white blood cells. On the other hand, when j is equal to or greater than N in Step S311 (Yes in Step S311), the control section 726 completes the process.

After the above Step S326, the CPU 731*a* stands by to receive the blood cell image (No in Step S327 of FIG. 14A). When the blood cell image transmitted from the microscope unit 71 is received by the communication interface 731*h* of the image processing unit 73 (Yes in Step S327), the CPU 731*a* performs a correction process on the received blood cell image (Step S328) and stores the blood cell image after the correction in the hard disk 731*d* (Step S329). In the process of Step S329, a white blood cell ID corresponding to the blood cell image is generated, and the blood cell image is stored as image data with a file name including the white blood cell ID.

Next, the CPU 731*a* specifies areas of cytoplasm and a nucleus in the blood cell image (Step S330). In a stained white blood cell, a nucleus has a color different from that of a cytoplasm. Moreover, the colors of the cytoplasm and the nucleus of the white blood cell are different from the colors of a red blood cell and a background. Accordingly, in the process of Step S330, a nucleus area and a cytoplasm area which are included in a white blood cell image are specified by using a RGB value of the white blood cell image.

Next, the CPU 731*a* calculates various characteristic parameters of the white blood cell on the basis of the blood cell image (Step S331). The characteristic parameters include the area of a white blood cell nucleus, the number of nuclei, irregularity, the tone and concentration (unevenness) of a white blood cell nucleus, the area, tone and concentration (unevenness) of white blood cell cytoplasm, and the area ratio and the concentration ratio between the nucleus and the cytoplasm, which can be obtained on the basis of color signals (G, B, R) of the image.

Next, using the obtained characteristic parameters, the CPU 731*a* identifies the type of the white blood cell (Step S332). Specifically, for example, several characteristic parameters of the white blood cell are sequentially compared with judgment criteria values, which are determined for the parameters in advance, to gradually narrow down the type of the white blood cell. In this manner, the imaged white blood cell is classified as a mature white blood cell such as a lymphocyte, a monocyte, an eosinophil, a basophil or a neutrophil (bacillary, lobulated), as an immature white blood cell such as a blast cell, a young granulocyte or an atypical lymphocyte, or as an erythroblast. In Step S332, the CPU 731*a* increments the count result (number) of the specimen database DB2*b* one by one in accordance with the type of the classified white blood cell, and recalculates the count result (%) in accordance with the incremented count result (number).

Next, in Step S333, the CPU 731*a* determines whether the identified blood cell type is included in the review items determined in Step S324 (Step S333). When the blood cell type is included in the review items (Yes in Step S333), the CPU 731*a* sets the blood cell image as a display object (Step S334), stores data indicating that the blood cell image is the display object in the RAM 731*c*, and performs a process of Step S335. On the other hand, in Step S333, when the blood cell type is not included in the review items (No in Step S333), the CPU 731*a* performs the process of Step S335.

In Step S335, the CPU 731*a* determines whether the required counted number of the white blood cells has been satisfied, that is, whether i is equal to or greater than N (Step S335). When i is less than N (No in Step S335), the CPU increments i by 1 (Step S336), returns the process to Step S327, and stands by to receive another blood cell image.

On the other hand, when i is equal to or greater than N in Step S335 (Yes in Step S335), the CPU 731*a* registers the information relating to the specimen, the classification result, the data indicating the blood cell image as the display object, and the count result of the image processing unit 73, which are obtained as described above, in the specimen database DB1 and the blood cell database DB2 of the hard disk 731*d* (Step S337) and completes the process. More specifically, the information on the specimen such as the specimen ID received in Step S323, the patient's name, the patient's sex, hospital ward information, and comments is registered on the specimen database DB1. Further, the count result obtained by counting the blood cells by the blood cell counting apparatus 5, and the classification result such as the abnormality information are also registered on the specimen database DB1. In addition, the data indicating whether or not the blood cell image is the display object and the count result obtained by counting the blood cells by the image processing unit 73 are registered on the blood cell database DB2.

<Operation of Displaying Blood Cell Image>

Figure 17A:
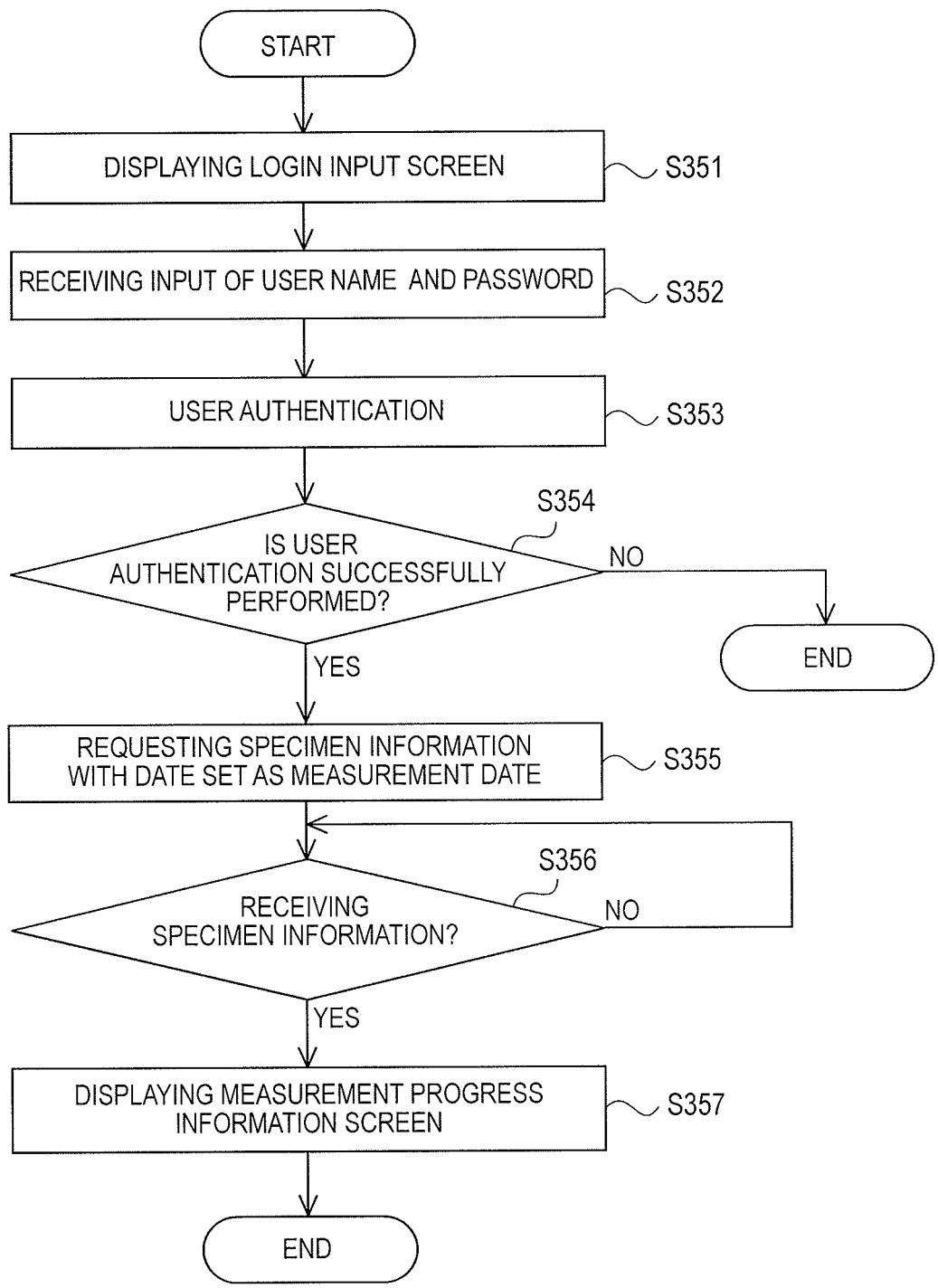
FIG. 17A is a flowchart showing the procedure of an initialization operation of the blood cell image display unit in a blood cell image display operation.
Figure 17B:
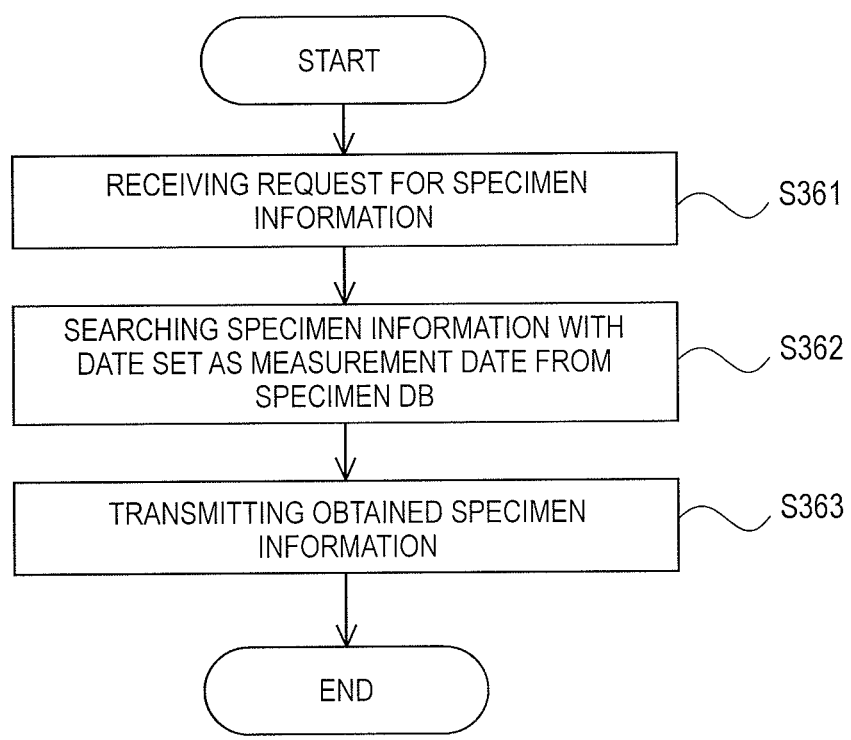
FIG. 17B is a flowchart showing the procedure of a specimen information transmitting operation of the image processing unit in the blood cell image display operation.

FIG. 17A is a flowchart showing the procedure of an initialization operation of the blood cell image display unit 75 in a blood cell image display operation, and FIG. 17B is a flowchart showing the procedure of a specimen information transmitting operation of the image processing unit 73 in the blood cell image display operation. The user operates the input section 753 of the computer 75*a* to instruct the execution of the blood cell image display program 754*a*. The CPU 751*a* of the computer 75*a* receives the instruction and executes the blood cell image display program 754*a*. In this manner, the computer 75*a* functions as the blood cell image display unit 75.

Immediately after the initiation of the blood cell image display program 754*a*, a login input screen prompting the input of a user name and a password is displayed (Step S351 of FIG. 17A). The user inputs the user name and the password in the login input screen (Step S352). The blood cell image display program 754*a*, which is executed by the CPU 751*a* of the blood cell image display unit 75, is an event-driven program, and in the CPU 751*a*, a process of Step S353 is invoked when an event occurs in which the user name and the password are input.

In Step S353, the CPU 751*a* performs a user authentication process. When the user authentication fails (No in Step S354), the CPU 751*a* completes the process. When the user is successfully authenticated by using the login process (Yes in Step S354), the CPU 751*a* transmits request data of specimen information with the date set as the measurement date to the image processing unit 73 via the communication interface 751*g* (Step S355).

The request data transmitted from the blood cell image display unit 75 is received by the communication interface 731*h* of the image processing unit 73 (Step S361 of FIG. 17B). In the CPU 731*a*, a process of Step S362 is invoked when an event occurs in which the request data is received.

In Step S362, from the specimen database DB1, the CPU 731*a* obtains the specimen information with the date set as the measurement date (Step S362). Next, the CPU 731*a* transmits the obtained specimen information to the blood cell image display unit 75 via the communication interface 731*g* (Step S363) and completes the process.

After transmitting the request data of specimen information, the CPU 751*a* of the blood cell image display unit 75 stands by to receive the specimen information (No in Step S356 of FIG. 17A). When the specimen information transmitted from the image processing unit 73 is received by the communication interface 751*g* of the blood cell image display unit 75 (Yes in Step S356), a measurement progress screen (not shown) is displayed (Step S357) and the process is completed. In the measurement progress screen, the specimen information relating to plural specimens is displayed as a list. In the measurement progress screen, the user can select one of the pieces of specimen information displayed as a list. By selecting one piece of specimen information and subsequently performing a predetermined operation (for example, the double-clicking of the left button of a mouse), it is possible to provide an instruction for displaying a blood cell image relating to the specimen.

Figure 18A:
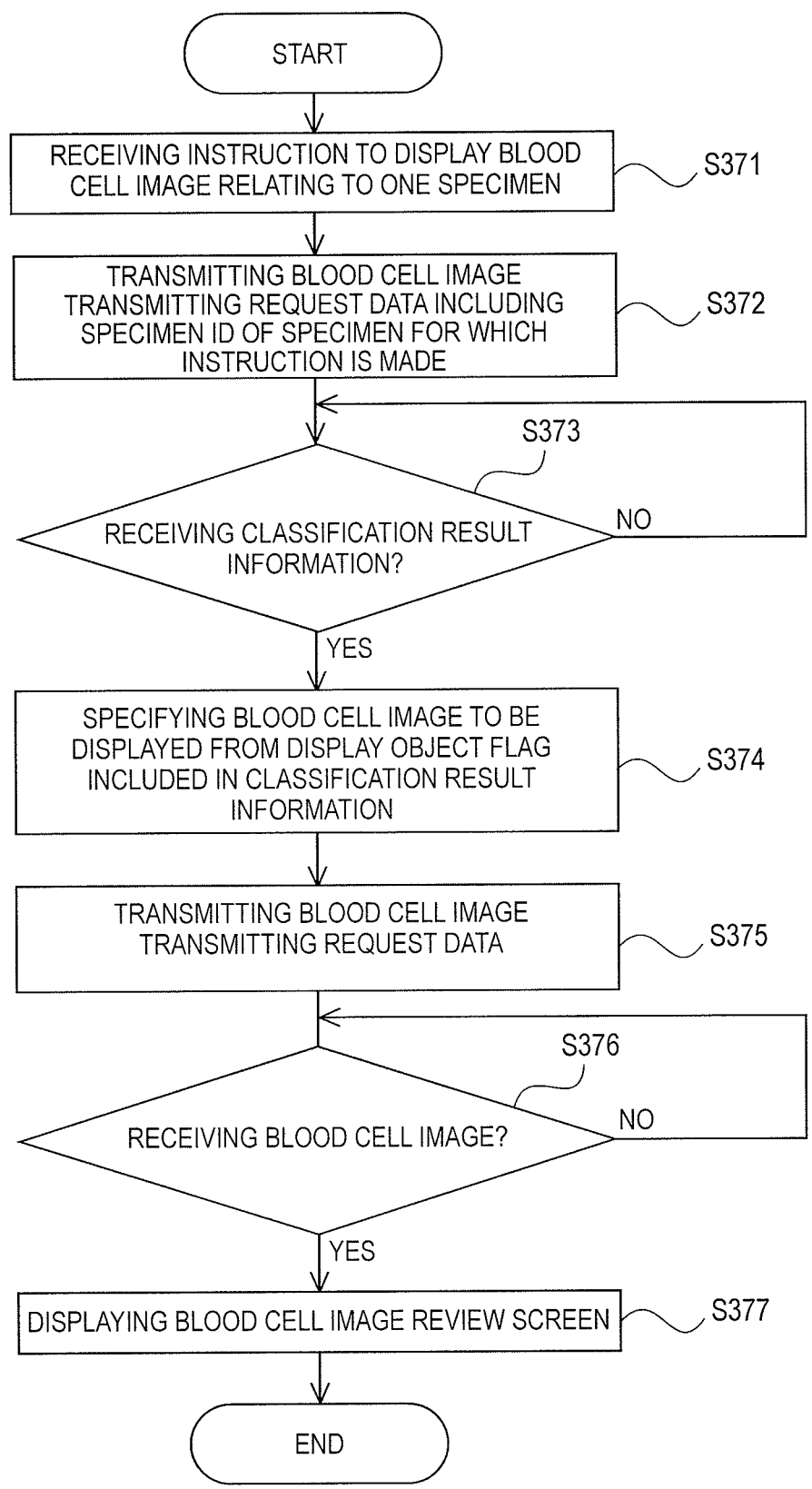
FIG. 18A is a flowchart showing the procedure of an image display operation of the blood cell image display unit in the blood cell image display operation.
Figure 18B:
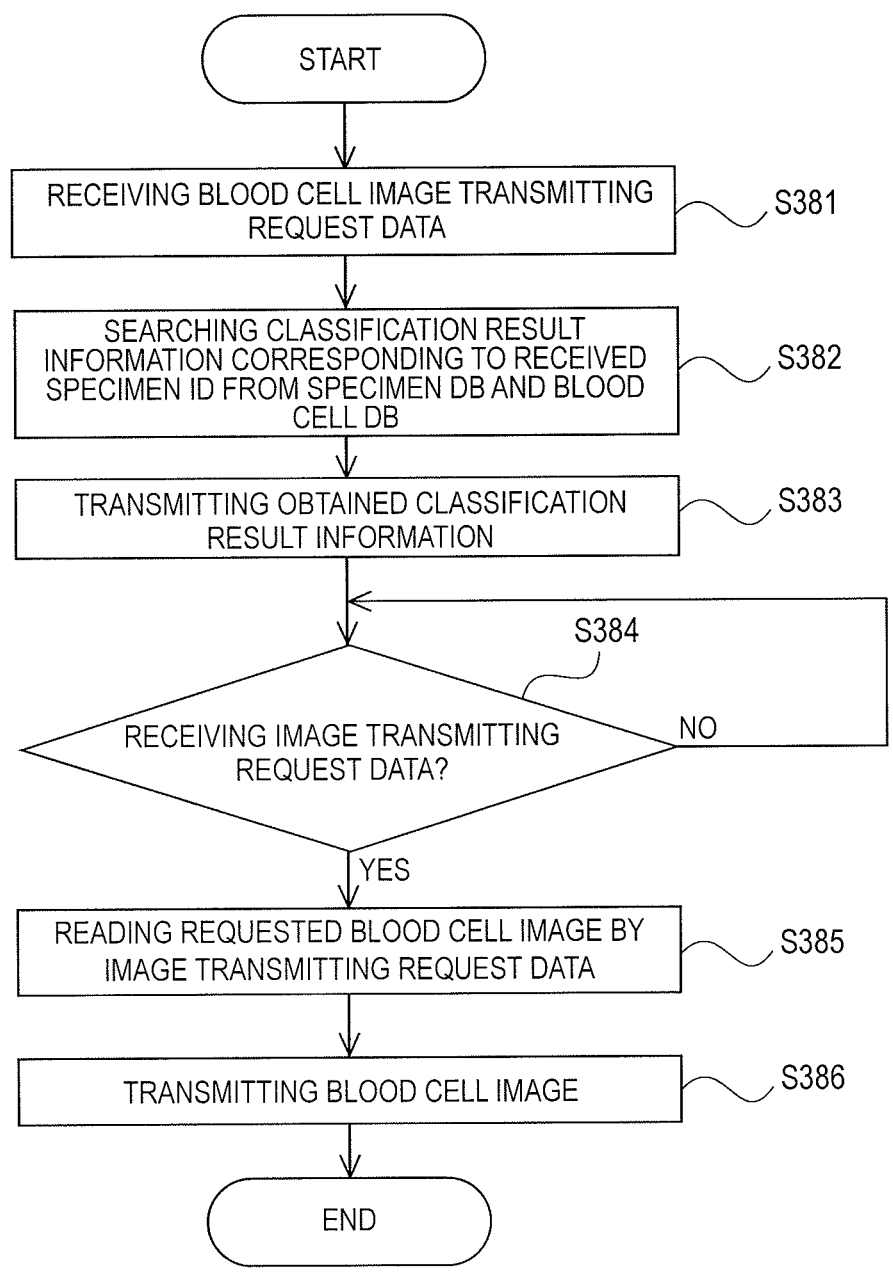
FIG. 18B is a flowchart showing the procedure of a blood cell image transmitting operation of the image processing unit in the blood cell image display operation.

FIG. 18A is a flowchart showing the procedure of an image display operation of the blood cell image display unit 75 in the blood cell image display operation, and FIG. 18B is a flowchart showing the procedure of a blood cell image transmitting operation of the image processing unit 73 in the blood cell image display operation. In the blood cell image display unit 75, when an event occurs, in which the instruction for displaying the blood cell image relating to one specimen is received as described above, in a state in which the measurement progress screen is displayed (Step S371) a process of Step S372 is invoked.

In Step S372, the CPU 751*a* transmits blood cell image transmitting request data, including the specimen ID of the specimen for which the instruction is made, to the image processing unit 73 via the communication interface 751*g* (Step S372).

The request data transmitted from the blood cell image display unit 75 is received by the communication interface 731*h* of the image processing unit 73 (Step S381 of FIG. 18B). In the CPU 731*a*, a process of Step S382 is invoked when an event occurs in which the request data is received.

In Step S382, the CPU 731*a* obtains classification result information from the specimen database DB1 and the blood cell database DB2 corresponding to the specimen ID (Step S382). The classification result information includes the count result obtained by the blood cell counting apparatus 5, white blood cell IDs specifying the white blood cells, the types (monocyte, neutrophil, basophil, eosinophil, lymphocyte, etc.) as the result of the white blood cell classification, information (display image flag) indicating whether or not the blood cell image is a display image, the count result (number) relating to each blood cell type, and a ratio (count result (%)) of the number of each blood cell type to the total number of the white blood cells.

Next, the CPU 731*a* transmits the obtained classification result information to the blood cell image display unit 75 via the communication interface 731*g* (Step S383).

After transmitting the request data of the classification result information, the CPU 751*a* of the blood cell image display unit 75 stands by to receive the classification result information (No in Step S373 of FIG. 18A). When the classification result information transmitted from the image processing unit 73 is received by the communication interface 751*g* of the blood cell image display unit 75 (Yes in Step S373), the blood cell image to be displayed is specified by the display object flag (Step S374), and the image transmitting request data requesting the transmitting of the specified blood cell image is transmitted to the image processing unit 73 via the communication interface 751*g* (Step S375).

After transmitting the classification result information, the CPU 731*a* of the image processing unit 73 stands by to receive the image transmitting request data (No in Step S384 of FIG. 18B). When the request data transmitted from the blood cell image display unit 75 is received by the communication interface 731*h* of the image processing unit 73 (Yes in Step S384), the CPU 731*a* reads the blood cell image (after-correction blood cell image) requested by the image transmitting request data from the folder corresponding to the specimen ID in the blood cell image folder 735 in the hard disk 731*d* (Step S385), transmits the read blood cell image to the blood cell image display unit 75 via the communication interface 731*g* (Step S386), and completes the process.

After transmitting the image transmitting request data, the CPU 751*a* of the blood cell image display unit 75 stands by to receive the blood cell image (No in Step S376 of FIG. 18A). When the blood cell image transmitted from the image processing unit 73 is received by the communication interface 751*g* of the blood cell image display unit 75 (Yes in Step S376), a blood cell image review screen is displayed (Step S377) and the process is completed.

Figure 19:
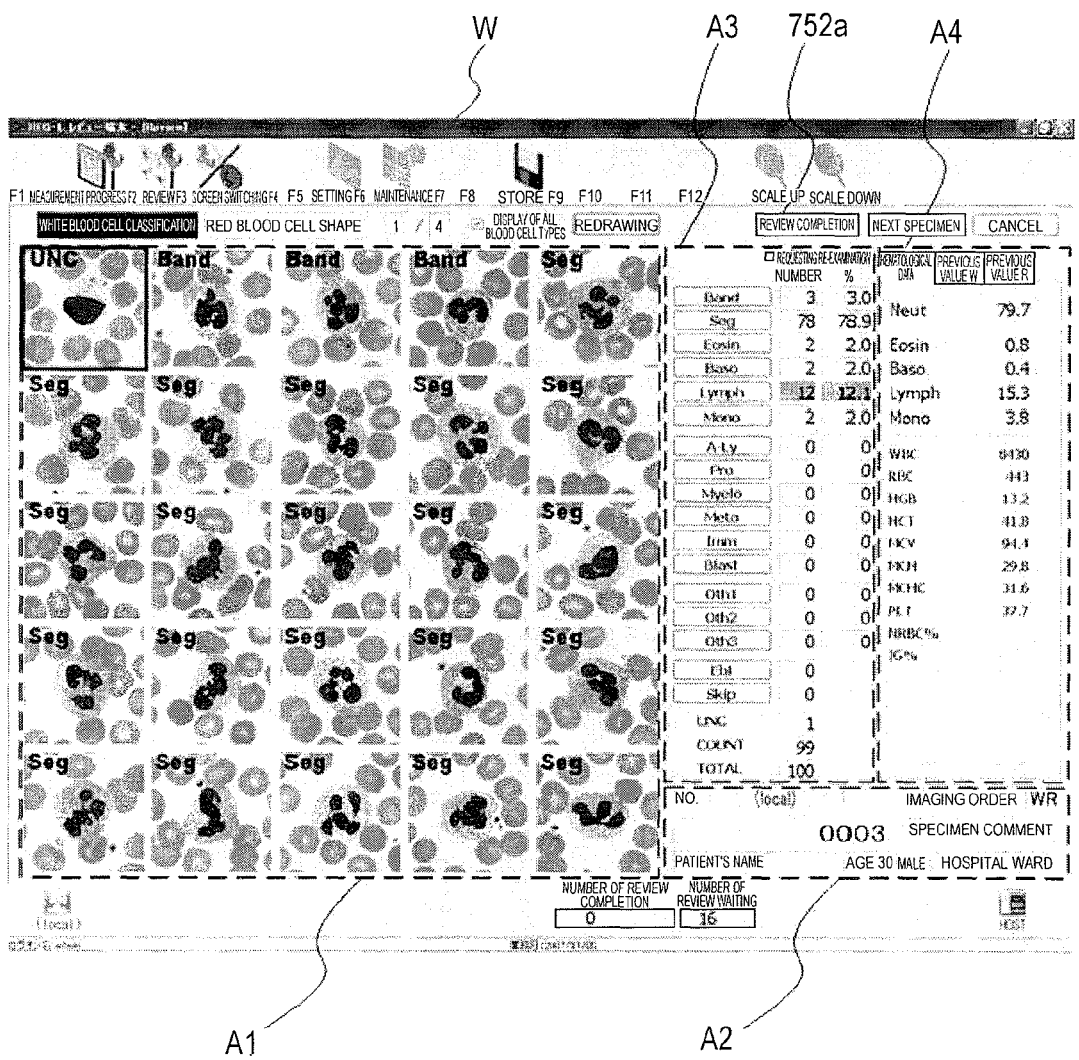
FIG. 19 is a diagram showing an example of a blood cell image review screen.

FIG. 19 is a diagram showing an example of the blood cell image review screen. In a blood cell image review screen W, a blood cell image display area A1 for displaying one or more blood cell images, a patient information display area A2 for displaying patient information, a counted value display area A3 for displaying the result of the counting of each type of classified blood cells, and an analysis result display area A4 for displaying the analysis result of the blood cell counting apparatus 5 are included. In the blood cell image display area A1, images which are obtained by reducing received blood cell images are displayed as a list. A blood cell type is displayed with a string of characters ("Mono" for a monocyte, "Neut" for a neutrophil, "EO" for an eosinophil, "Baso" for a basophil, "Lymp" for a lymphocyte, etc.) in each reduced image. In addition, only the blood cell image which is determined as the display object in Step S334 is displayed in the blood cell image display area A1, and the other blood cell images are not displayed. As a result, it is possible to display any type of the blood cell image alone, and there is no need to confirm the blood cell images which are a type not requiring review by the user of the blood cell image classifying apparatus 7. Accordingly, the review of the blood cell image is performed with efficiency.

In the counted value display area A3 of the blood cell image review screen W, plural buttons, each of which has a character string of a name of a blood cell type displayed therein, are arranged. These buttons can be selected by clicking the left button of a mouse. In a state in which a blood cell image is selected (the blood cell image can also be selected by clicking the left button of the mouse), the user selects a button of a desired blood cell type so that the blood cell image can be classified as the blood cell type. In addition, the count result (number) and the count result (%), which are registered on the blood cell data base DB2*b* and received by the CPU 751*a* of the blood cell display unit in Step S373, are displayed in the counted value display area A3.

On the other hand, the count result of the blood cell counting apparatus 5, which is registered on the specimen database DB1 and included in the classification result information received by the CPU 751*a* of the blood cell image display unit in Step S373, is displayed in the analysis result display area A4.

Figure 18C:
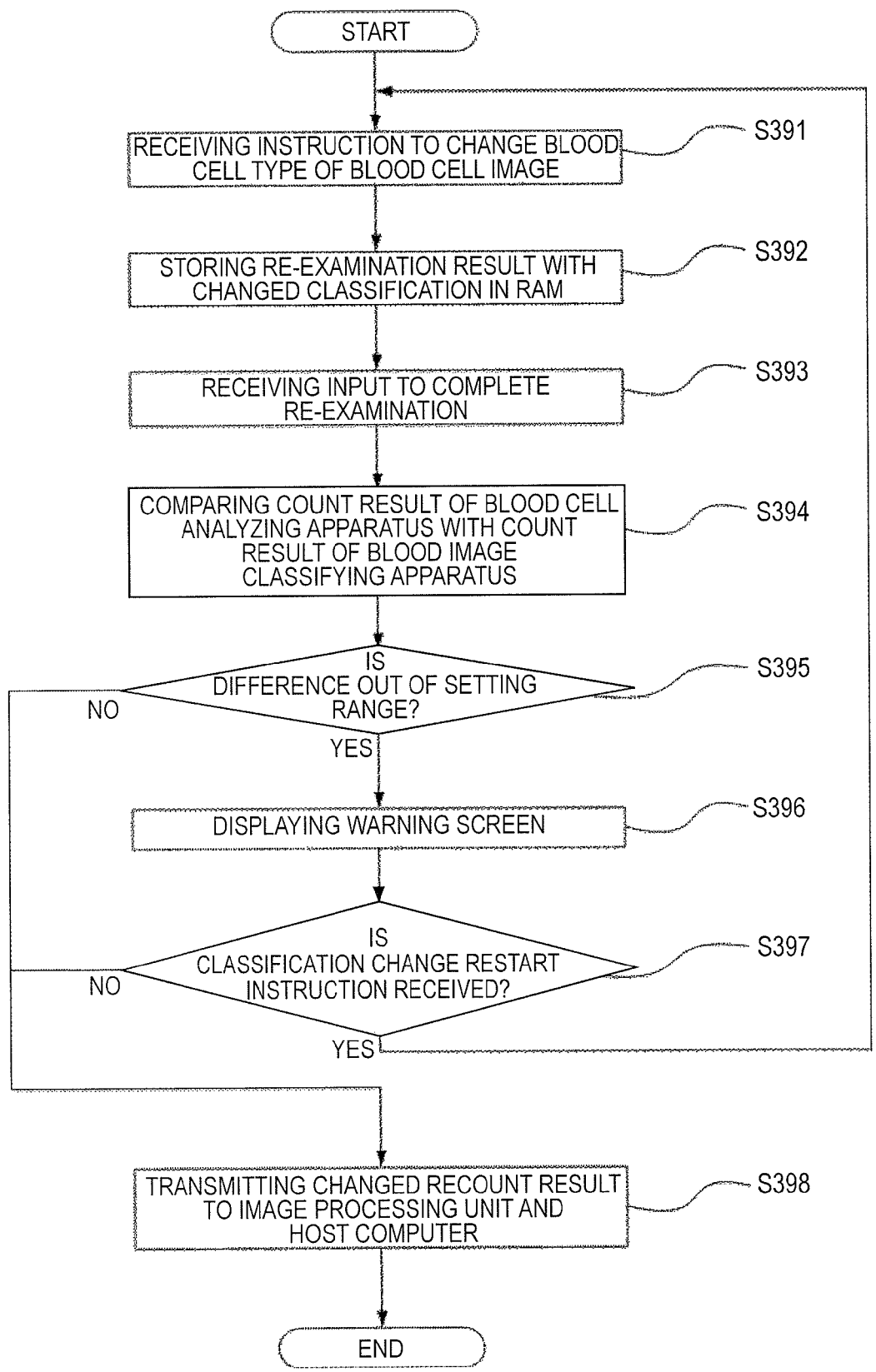
FIG. 18C is a flowchart showing the flow of a recount result registration operation of a blood cell image display unit in the blood cell image display operation.

FIG. 18C is a flowchart showing the flow of a recount result registration operation of the blood cell image display unit 75. As described above, in a state in which the blood cell image review screen is displayed, when input is received to change a blood cell type of a blood cell image (Step S391), the CPU 751*a* stores a recount result with the changed classification in the RAM 751*c* (Step S392). After that, when input is provided to the CPU 751*a* by clicking a review completion button 752*a* provided in the blood cell image review screen to complete the re-examination (Step S393), the CPU 751*a* compares the count result (%) which is displayed in the counted value display area A3 with the count result which is displayed in the analysis result display area A4 (Step S394). When the absolute value of the difference between two count results exceeds a predetermined value range which is stored in the warning output range table WT in advance (YES in Step S395), the CPU 751*a* causes the image display section 752 to display the warning screen (Step S396). Further, the warning screen is output not only for the blood cell type which is set to the display object, but also for the blood cell type which is not set to the display object on the blood cell image review screen W. In addition, the objects for comparison in Step S394 are the same type of the blood cells. However, as to Band and Seg, the CPU 751*a* compares the sum of Band and Seg among the count results (%) which are displayed in the counted value display area A3 with Neut (neutrophil) among the count results which are displayed in the analysis result display area A4.

Further, the predetermined value ranges stored in the warning output range table WT which is used in Step S395 are set for each blood cell type. For example, in a case of Neut (neutrophil), the predetermined value range may be set to ±20%, and in a case of Eosin (eosinophil), ±5%.

Figure 23:
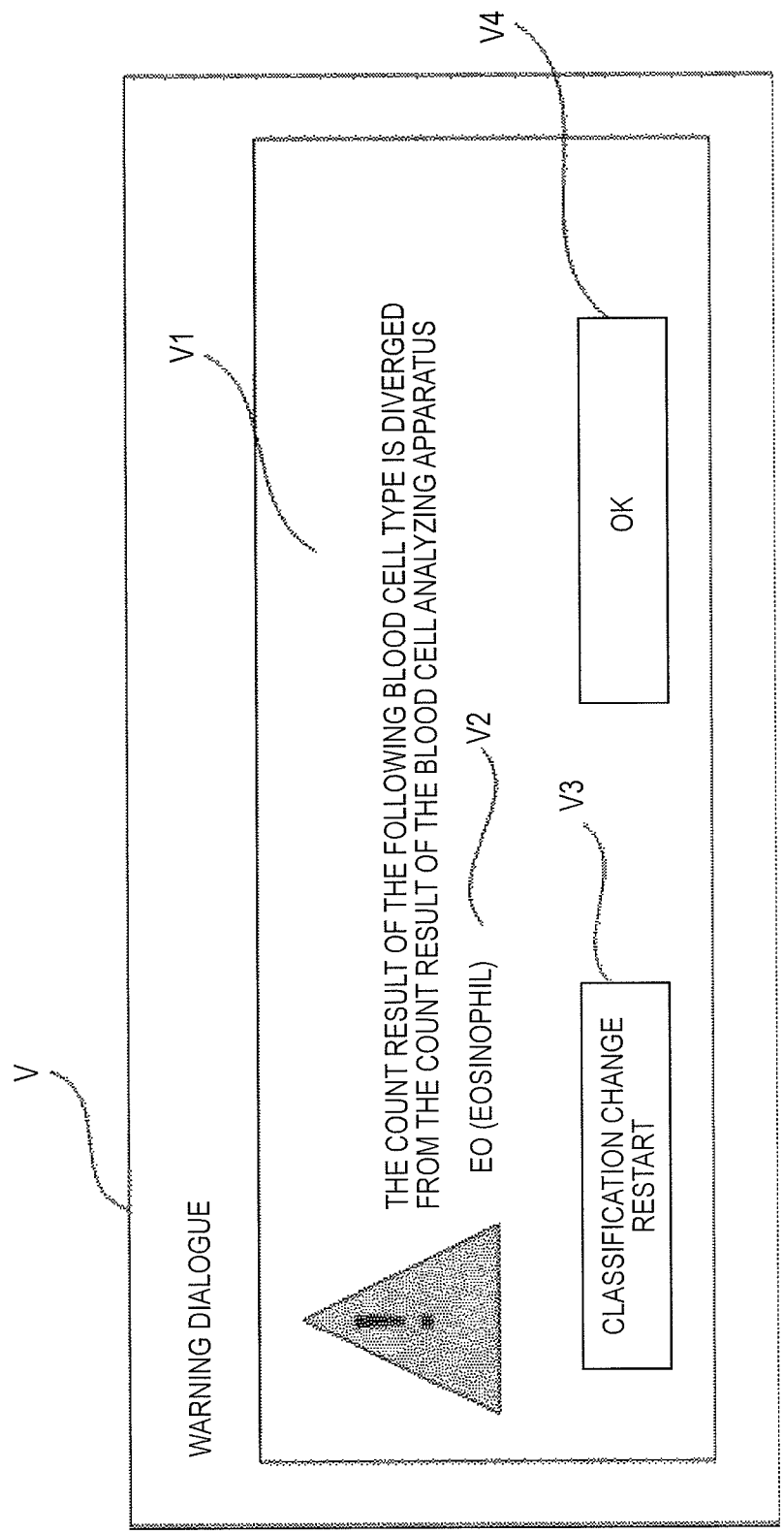
FIG. 23 is a diagram showing an example of a warning screen.

FIG. 23 shows the warning screen V which is displayed in the image display section 752 in Step S396. As shown in the drawing, in the warning screen V, a warning display area V1 which is used to warn the user that the count result of the blood cell image classifying apparatus 7 is diverged, in respect of the same specimen, from the count result of the blood cell counting apparatus 5, a blood cell display area V2 which is used to display the type of the blood cell in which the count results are diverged from each other, a classification change restart button V3 which is used to restart the classification change of the blood cell type by the blood cell image review screen W without starting the registration of the count results on the host computer 9, and an OK button V4 which is used to register the count results on the host computer after it is recognized that the count results are diverged from each other.

When the classification change restart button V3 is selected (YES in Step S397), the CPU 751*a* returns the process to Step S391 and restarts the classification change. On the other hand, when the OK button V4 is selected (NO in Step S397), the CPU 751*a* transmits the recount result, including the value counted for each blood cell type, which reflects the changed classification result to the image processing unit 73 and the host computer 9 via the communication interface 751*g* (Step S398), and completes the process. The recount result is received by the image processing unit 73 and the host computer 9 to be registered in the blood cell database DB2 of the image processing unit 73 and to be stored in the hard disk of the host computer 9. In addition, when the absolute value of the difference between the count results is in the predetermined value range which is stored in the warning output range table WT in Step S395 (NO in Step S395), the CPU 751*a* skips the processes of Step S396 and Step S397, and proceeds to the process of Step S398. Further, the value range used in Step S395 is set for each blood cell type. In addition, the value range can be arbitrarily set by the user of the blood cell image classifying apparatus 7, but it may be set to a fixed value range in advance.

<Operation of Changing Setting of Review Item>

Figure 20A:
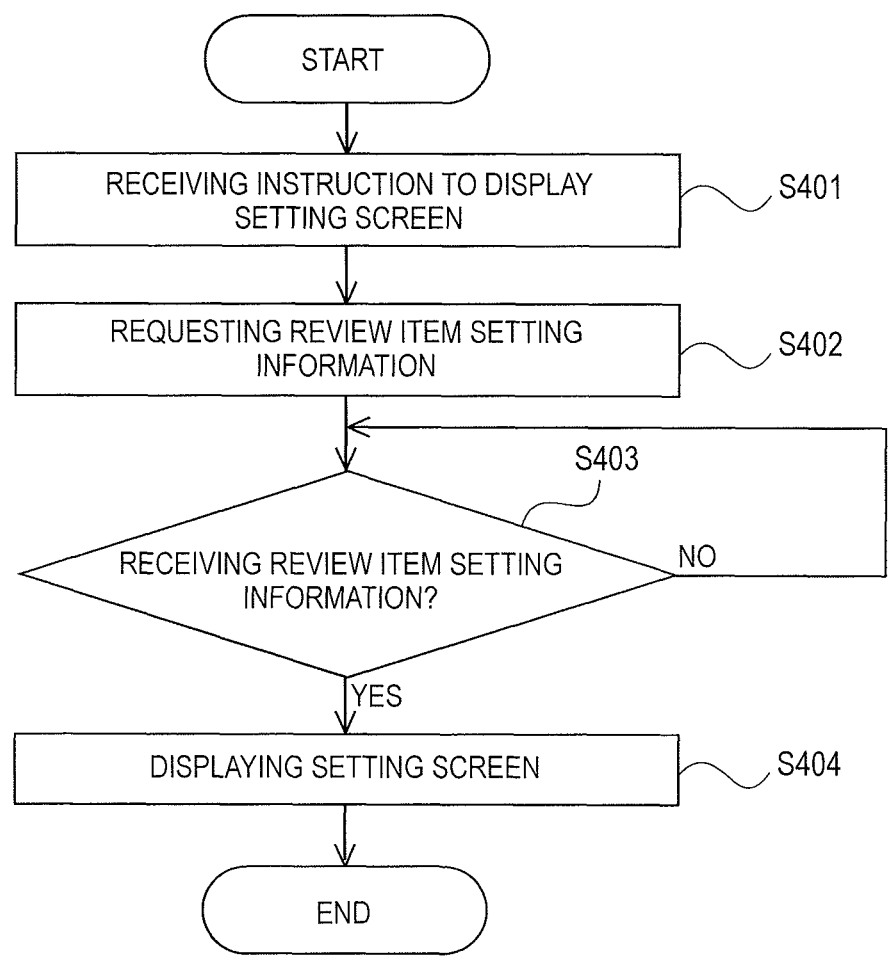
FIG. 20A is a flowchart showing the flow of a setting screen display operation of the blood cell image display unit in a review item changing operation.
Figure 20B:
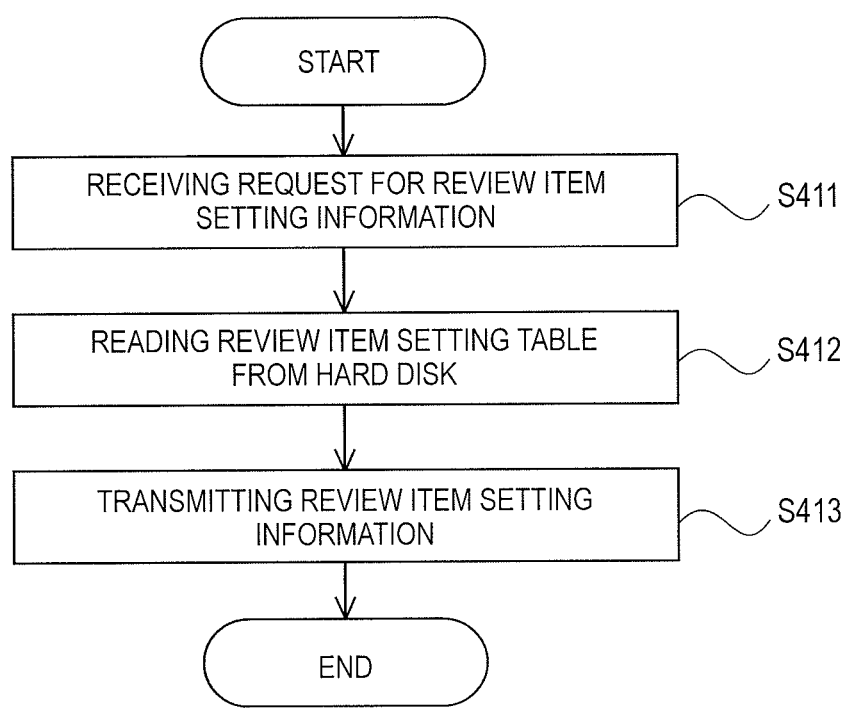
FIG. 20B is a flowchart showing the flow of a review item setting information transmitting operation of the image processing unit in the review item changing operation.

As described above, the setting of the review item setting table TBL can be changed. FIG. 20A is a flowchart showing the flow of a setting screen display operation of the blood cell image display unit 75 in a review item changing operation, and FIG. 20B is a flowchart showing the flow of a review item setting information transmitting operation of the image processing unit 73 in the review item changing operation. In the blood cell image display unit 75, in a state in which the measurement progress screen is displayed, a setting screen display instruction can be received by clicking a setting button (not shown) disposed in an upper area in the screen with the left button of a mouse. In the CPU 751*a*, a process of Step S402 is invoked when an event occurs in which the setting screen display instruction is received (Step S401 of FIG. 20A).

In Step S402, the CPU 751*a* transmits review item setting information transmitting request data to the image processing unit 73 via the communication interface 751*g* (Step S402).

The request data transmitted from the blood cell image display unit 75 is received by the communication interface 731*h* of the image processing unit 73 (Step S411 of FIG. 20B). In the CPU 731*a*, a process of Step S412 is invoked when an event occurs in which the request data is received.

In Step S412, the CPU 731*a* reads the review item setting table TBL from the hard disk 731*d* (Step S412). Next, the CPU 731*a* transmits review item setting information indicating the contents of the review item setting table TBL to the blood cell image display unit 75 via the communication interface 731*g* (Step S413) and completes the process.

After transmitting the review item setting information request data, the CPU 751*a* of the blood cell image display unit 75 stands by to receive the review item setting information (No in Step S403 of FIG. 20A). When the review item setting information transmitted from the image processing unit 73 is received by the communication interface 751*g* of the blood cell image display unit 75 (Yes in Step S403), the CPU 751*a* displays a setting screen (Step S404) and completes the process.

Figure 21:
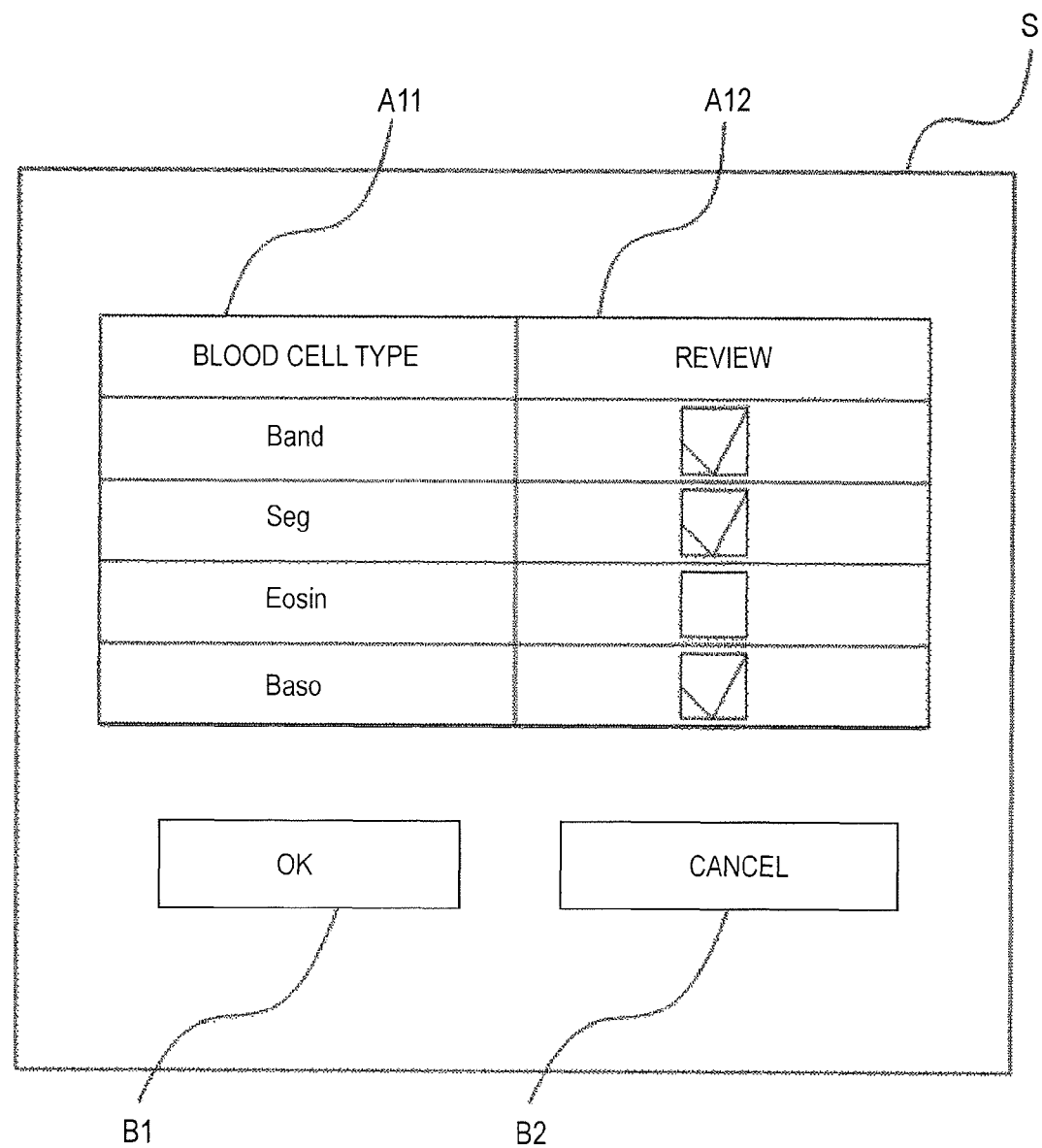
FIG. 21 is a diagram showing an example of a setting screen.

FIG. 21 is a diagram showing an example of the setting screen. As shown in FIG. 21, in the setting screen S, a blood cell type field A11 indicating the blood cell type, a setting field A12 which is used to set whether or not each blood cell type becomes the display object, a OK button B1 which is used to register the setting of the display object and to complete the setting, and a cancel button B2 which is used to stop the setting of the display object and to complete the display of the setting screen S are displayed. Each check box of the setting field A12 can be checked with a check mark or cleared by clicking the left button of a mouse, and the blood cell types with the check mark become the display objects.

Figure 20C:
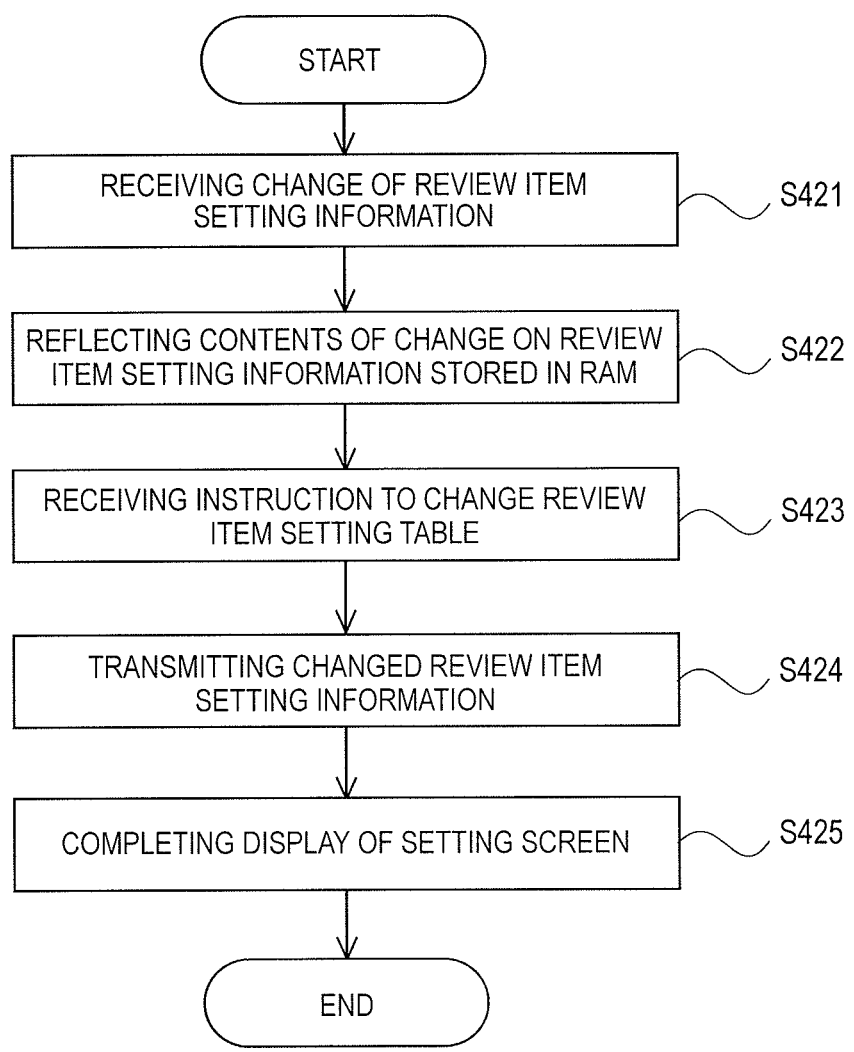
FIG. 20C is a flowchart showing the flow of an operation of accepting a change in review item setting by the blood cell image display unit in the review item changing operation.
Figure 20D:
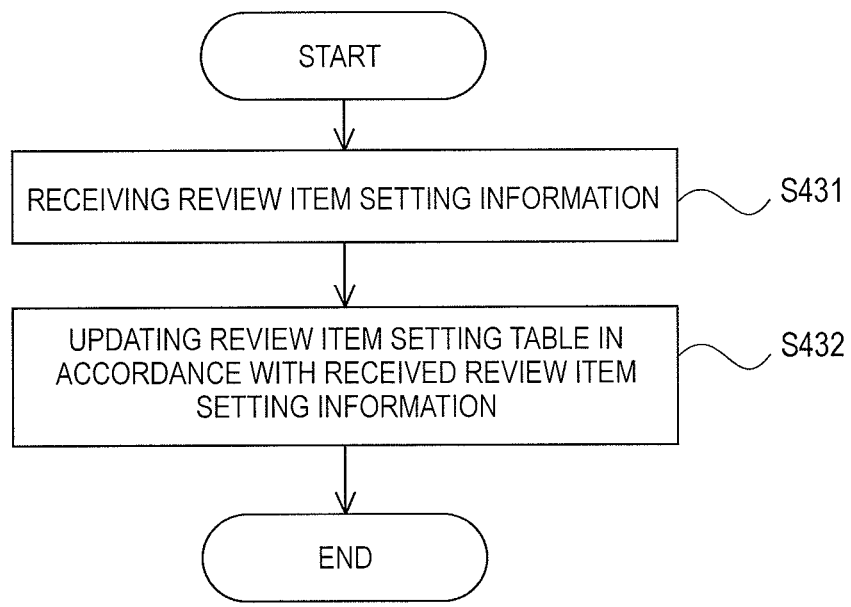
FIG. 20D is a flowchart showing the flow of an operation of updating the review item setting table by the image processing unit in the review item changing operation.

FIG. 20C is a flowchart showing the flow of an operation of accepting a change in review item setting by the blood cell image display unit 75 in the review item changing operation, and FIG. 20D is a flowchart showing the flow of an operation of updating the review item setting table by the image processing unit 73 in the review item changing operation. As described above, when the blood cell image display unit 75 receives input from the user to change the review item setting information (Step S421 of FIG. 20C), the CPU 751a reflects the contents of the change in the review item setting information of the RAM 751c (Step S422). Then, when an instruction for updating the review item setting table TBL is received due to the selection of the OK button B1 (Step S423), the CPU 751a transmits the review item setting information stored in the RAM 751c to the image processing unit 73 via the communication interface 751g (Step S424), completes the display of the setting screen W (Step S425), and completes the process.

The review item setting information transmitted from the blood cell image display unit 75 is received by the communication interface 731h of the image processing unit 73 (Step S431 of FIG. 20D). In the CPU 731a, a process of Step S432 is invoked when an event occurs in which the review item setting information is received.

In Step S432, the CPU 731a updates the review item setting table TBL in accordance with the received review item setting information (Step S432) and completes the process. In this manner, the setting of the review item, which has been changed and input by the user, is reflected in the review item setting table TBL.

<Shutdown Operation>

Figure 22A:
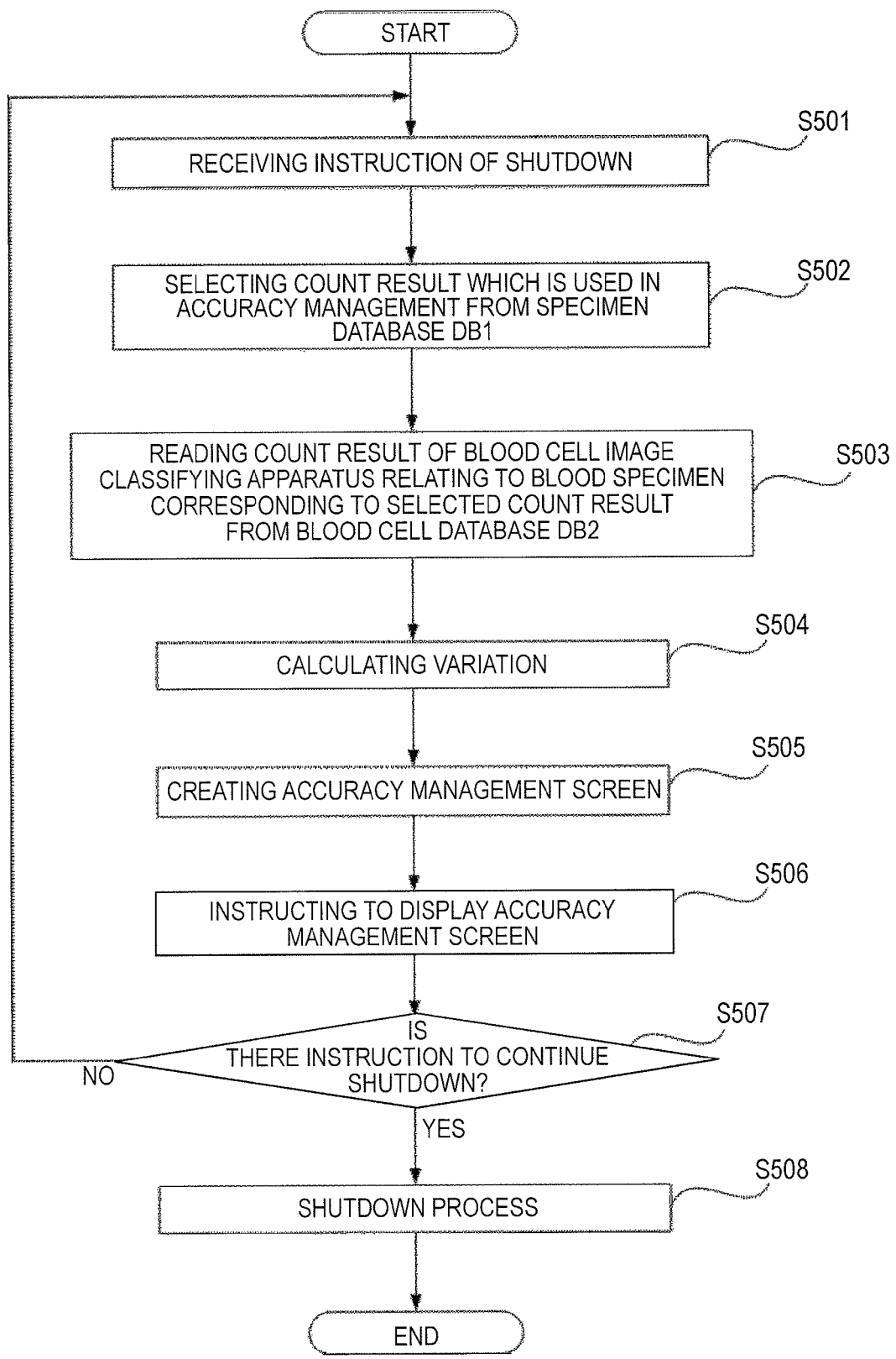
FIG. 22A is a flowchart showing the procedure of an operation of the image processing unit in a shutdown operation.
Figure 22B:
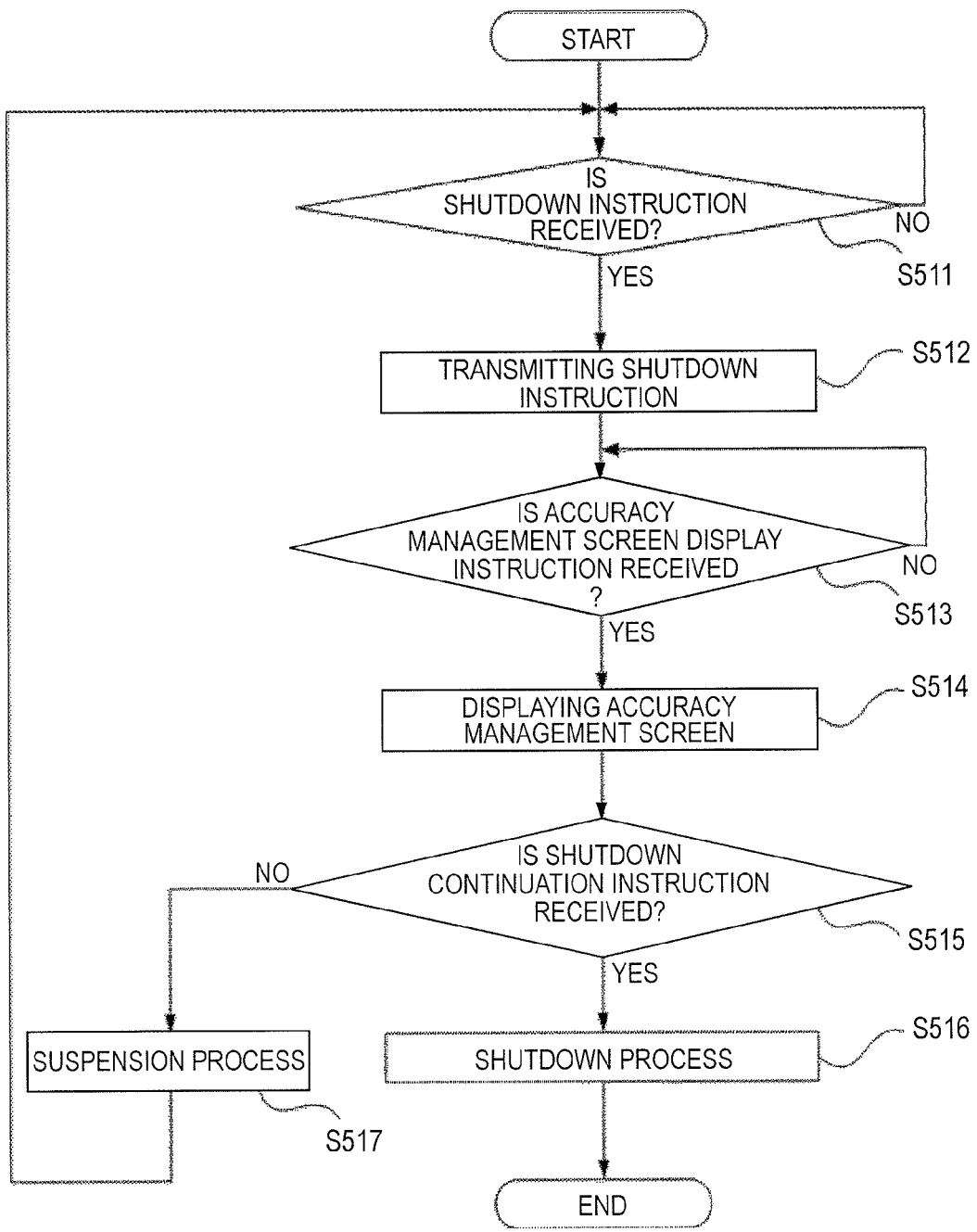
FIG. 22B is a flowchart showing the procedure of an operation of the image display unit in the shutdown operation.

Next, a shutdown operation of the blood cell image classifying apparatus 7 will be described. The user operates the blood cell image display unit 75, so that the shutdown operation is performed. When the blood cell image classifying apparatus 7 is shut down, the image processing unit 73 automatically performs the accuracy management in order to confirm that the count result of the blood cell image classifying apparatus 7 has been correctly obtained. FIG. 22A is a flowchart showing the operation procedure of the image processing unit 73 in the shutdown operation. FIG. 22B is a flowchart showing the operation procedure of the image display unit 75 in the shutdown operation.

When the CPU 751a of the blood cell image display unit 75 receives a shutdown starting process instruction which is caused by the user pressing the shutdown starting button (not shown) (YES in Step S511), the CPU 751a transmits a signal instructing to start the shutdown to the image processing unit 73 (Step S512). When receiving the instruction signal to start the shutdown from the CPU 751a (Step S501), the CPU 731a of the image processing unit 73 performs a process of selecting the count result to be used in the accuracy management from the specimen database DB1 (Step S502). In this process, the CPU 731a selects all the specimens which have the date set as the measurement date of the measurement date field F15 of the specimen database DB1, and selects the specimens from the selected specimen to 20 specimens which match the selection condition registered on the selection condition table QCT. At this time, as the selection condition, it is preferable that the condition in which all of a neutrophil, a lymphocyte, a monocyte, an eosinophil, and a basophil are in a normal range which is shown in a healthy person, for example. The blood cell counting apparatus 5 is designed to correctly count at least the specimens of a healthy person, so that the accuracy in variation can be improved by mainly using the count result of the specimens of the healthy person.

Next, the CPU 731a reads the count results (%) of the specimen selected in Step S502 and all the specimens having the same specimen ID from the blood cell database DB2b (Step S503). Then, the CPU 731a calculates the variation for each blood cell type in accordance with the following Equation (Step S504).

$$\text{Variation}=(\text{Count Result 1}-\text{Count Result 2})/\text{Count Result 1}\times 100\%$$

(Here, the count result 1 is an average value for each blood cell type of the count result of the specimen selected in Step S502, and the count result 2 is an average value for each blood cell type of the count result (%) read in Step S503. Further, the same count result of the same blood cell type is used for the count result 1 and the count result 2. However, regarding Band and Seg, the count result 1 is calculated by the average value of the count result of Neut (neutrophil), and the count result 2 is calculated by the sum of the average value of the count result of Band and the average value of the count result of Seg.)

The CPU 731a creates the accuracy management screen on the basis of the variation obtained in Step S504 (Step S505), and transmits the display instruction of the accuracy management screen to the blood cell image display unit 75 (Step S506). The CPU 751a of the blood cell image display unit 75 stands by the display instruction of the accuracy management screen (NO in Step S513). When the display instruction of the accuracy management screen is received (YES in Step S513), the CPU 751a displays the accuracy management screen on the image display section 752 (Step S514).

Figure 24:
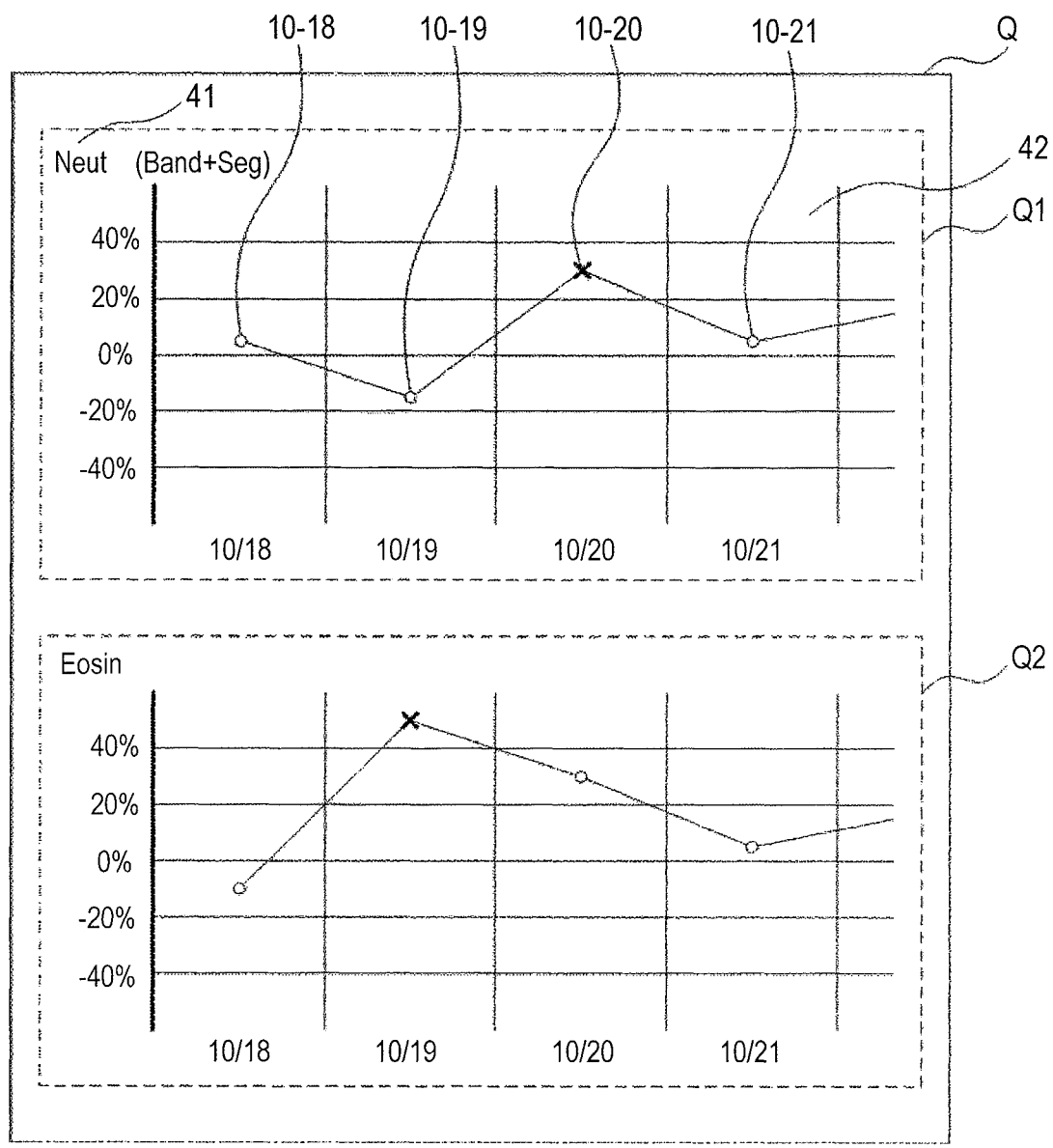
FIG. 24 is a diagram showing an example of an accuracy management screen.

FIG. 24 is a diagram showing the accuracy management screen which is displayed on the image display section 752. As shown in the drawing, in the accuracy management screen Q, graphs of the display areas Q1, Q2, . . . indicating the result of the accuracy management in chronological order are displayed for each blood cell. Each graph of the display area Q1, Q2, . . . is provided with a blood cell type area q1 indicating the blood cell type and a graph area q2 indicating the result of the accuracy management in chronological order. In the graph displayed in the graph area q2, the vertical axis is set to the variation, and the horizontal axis is set to the date. The center of the vertical axis in the vertical direction is set to 0 of variation, the upper portion of the center line shows a positive value of the variation (that is, the count result obtained by the blood cell counting apparatus 5 is larger than the count result obtained by the blood cell image classifying apparatus 7), and the lower portion of the center line shows a negative value of the variation (that is, the count result obtained by the blood cell counting apparatus 5 is smaller than the count result obtained by the blood cell image classifying apparatus 7). The variation obtained in Step S404 is plotted on a position according to the obtained value and the date, and displayed as plot 10-18, plot 10-19, plot 10-20, and plot 10-21. In addition, values showing a reference range of the variation are set in the image processing unit 73 for each blood cell type in order to determine whether or not the count result by the blood cell image classifying apparatus 7 is normally obtained. The variation departing from the reference range is plotted separate from the other plots. For example, regarding Neut (Band+Seg) as shown in FIG. 24, a reference range of the variation is set to ±0.2, the plot 10-20 at October 20th when the variation is larger than +20% is displayed with the x mark so as to be distinguished from the other plots. Similarly, regarding Eosin, the reference range of the variation is set to ±0.4, the plot at October 19th when the variation is larger than +40% is displayed with the x mark so as to be distinguished from the other plots. Further, the reference range can be arbitrarily set by the user of the blood cell image classifying apparatus 7, but it may be set to a fixed value range in advance. Further, the accuracy management screen Q is displayed not only with the blood cell type which is set to the display object, but also with the blood cell type which is not set to the display object on the blood cell image review screen W.

The user of the blood cell image classifying apparatus 7 who confirms the accuracy management screen determines whether the shutdown continues or the shutdown is suspended so as to perform the maintenance of the blood cell image classifying apparatus 7. In the image display section 752 of the blood cell image display unit 75, a screen (not shown) is displayed to select the continuation and the suspension of the shutdown. When the continuation of the shutdown is instructed (YES in Step S515), the CPU 752a shuts down the blood cell image display unit 75, and transmits the instruction that the shutdown continues to the blood cell image processing unit 73 (Step S516). When the suspension of the shutdown is instructed (NO in Step S515), the CPU 752a transmits the suspension instruction to the blood cell image processing unit 73, and suspends the shutdown by returning the process to Step S511 (Step S517).

When the continuation instruction of the shutdown is issued from the blood cell image displaying unit 75 (YES in Step S507), the CPU 732a shuts down the blood cell image processing unit 73, and transmits a signal to instruct the shutdown to the microscope unit 71 (Step S508). The control section 726 of the microscope unit 71 which receives the shutdown instruction shuts down the microscope unit 71. On the other hand, when the suspension instruction of the shutdown is issued from the blood cell image displaying unit 75 (NO in Step S507), the CPU 732a suspends the shutdown by returning the process to Step S501.

With a configuration such as the one described above, the accuracy management screen is displayed on the blood cell image classifying apparatus 7. Accordingly, the difference between the count result of the blood cell image classifying apparatus 7 and the count result of the blood cell counting apparatus 5 is confirmed, so that it is confirmed that the right count result is obtained by the blood cell image classifying apparatus 7, that is, the accuracy management can be performed. In general, since the blood cell counting apparatus 5 confirms whether the right count result is obtained or not by the accuracy management specimen, it is possible to confirm whether the count result of the blood cell image classifying apparatus 7 is right or not by confirming the difference with the count result of the blood cell counting apparatus 5 on the basis of the reference value with high reliability.

In addition, the variation is displayed in the accuracy management screen, so that the comparison is easy to perform with the case where there is no difference between the count result of the blood cell image classifying apparatus 7 and the count result of the blood cell counting apparatus 5. The blood cell image classifying apparatus 7 can easily confirm that the right count result is obtained.

In addition, the accuracy management screen displays the variation and the center line which shows the case where there is no difference between the count result of the blood cell image classifying apparatus 7 and the count result of the blood cell counting apparatus 5, so that the accuracy of the difference can be easily confirmed.

In addition, the variation is calculated on the basis of the count results of plural specimens, so that the variation can be calculated with high accuracy. Therefore, it is possible to realize the accuracy management with high accuracy.

In addition, when the blood cell image classifying apparatus 7 is in the shutdown, the accuracy management can be automatically performed. Therefore, the accuracy management can be started without performing any particular operation.

In addition, with a configuration such as the one described above, when the count result of the blood cells performed by the blood cell image classifying apparatus 7 is diverged from the count result of the blood cells performed by the blood cell counting apparatus 5, the warning screen is automatically output. Therefore, even though the count results of the blood cell image classifying apparatus 7 and the blood cell counting apparatus 5 are not compared with each other for each specimen, the user of the blood cell image classifying apparatus 7 can be made aware that the count results are diverged from each other, so that the examination can be efficiently performed.

In addition, when the warning screen is output, the screen is easily returned to the blood cell image review screen W by selecting the classification change button V3, so that the classification change can be visually performed with ease.

In addition, since the blood cell image which is the display object can be selected in the blood cell image review screen W, the review can be omitted for the blood cell type which is not required to be reviewed, the examination can be effectively achieved, and when the count results are diverged from each other, the warning is output even to the blood cell type which is omitted from review, so that it is possible to prevent the wrong count result relating to the blood cell type, which is omitted from review, from being registered on the host computer.

(Other Embodiments)

In the above-mentioned embodiments, the configuration has been described in which the blood smear which is prepared by the smear preparing apparatus 6 is configured to be automatically transmitted from the smear preparing apparatus 6 to the blood cell image display apparatus 7, but the invention is not limited thereto. The blood smear may be manually set to the blood cell image display apparatus 7 by the user.

In the above-mentioned embodiments, the configuration has been described in which, when the blood cell image classifying apparatus 7 is in the shutdown, the accuracy management is automatically performed, but the invention is not limited thereto. It may be configured such that an accuracy management starting screen is displayed by the image display unit 75 to start the accuracy management, and when the user issues the instruction to start the accuracy management, the accuracy management is started. In addition, in the above-mentioned embodiments, the configuration has been described in which the variation is displayed in the accuracy management screen, but the count result of the blood cell counting apparatus 5 and the count result of the blood cell image classifying apparatus 7 may each be plotted on the graph. In this case, the count result of the blood cell counting apparatus 5 is normally displayed above the center line, so that the difference between two count results is easily comprehended.

In addition, in the above-mentioned embodiments, only the specimens which match the selection condition stored in the selection condition table QCT are used for calculating the variation. However, the count results of all the specimens which have the date set as the measurement date may be used for calculating the variation.

In addition, in the above-mentioned embodiments, the calculation is carried out from the average of the plural count results of the blood cell counting apparatus 5 and the average of the plural count results of the blood cell image classifying apparatus 7. However, the calculation may be carried out from intermediate values of the plural count results. In addition, in the above-mentioned embodiments, the configuration has been described in which, by executing the image processing program, the computer functions as the image processing unit 73 to determine a blood cell image of a display object on the basis of the abnormality information of a specimen. However, the invention is not limited to this. A configuration may also be, in which the process of determining a blood cell image of a display object, the process of warning divergence in the count result, and the accuracy management process, is performed using dedicated hardware such as FPGA, ASIC or the like capable of executing the same process as the image processing program.

In the above-described embodiments, the configuration has been described in which a blood cell image is displayed by the blood cell image display unit 75 which is provided independently of the image processing unit 73. However, the invention is not limited to this. A configuration may be employed in which, by one unit having the function of the image processing unit 73 as well as the function of the blood cell image display unit 75, a blood cell image of a display object is determined on the basis of the abnormality information of a specimen and the determined blood cell image is displayed. Also, a configuration may be employed in which, by one unit having the functions of the microscope unit 71, the image processing unit 73 and the blood cell image display unit 75, the imaging of a slide glass, the reception of the specimen analysis result of the blood cell analyzing apparatus 5, the warning of the count result divergence and the accuracy management are performed.

In the above-described embodiments, the configuration has been described in which all the processes of the image processing program 734a are executed by the single computer 73a. However, the invention is not limited to this. A distribution system also can be employed for distributing the same processes as the above-described image processing program 734a to plural apparatuses (computers) and executing the processes.

In the above-described embodiments, the configuration has been described in which all the processes of the blood cell image display program 754a are executed by the single computer 75a. However, the invention is not limited to this. A distribution system also can be employed for distributing the same processes as the above-described blood cell image display program 754a to plural apparatuses (computers) and executing the processes.

What is claimed is:

1. A specimen processing system comprising:
a blood cell counting apparatus configured to count white blood cells for each subclass by measuring a blood specimen flowing in a flow cell; and
a blood cell image classifying apparatus, which is connected to the blood cell counting apparatus so as to perform data communication therewith, and which is configured to count white blood cells for each subclass on the basis of a blood cell image obtained by imaging a blood smear,
wherein the blood cell counting apparatus comprises an optical detecting section including an optical sensor;
wherein the blood cell image classifying apparatus comprises a microscope unit which comprises an objective lens, an XY stage, and a charge-coupled device (CCD) camera, and
wherein the blood cell image classifying apparatus further comprises a controller including a memory under control of a processor, the memory storing instructions enabling the processor to carry out operations, comprising:
receiving a first count result of a predetermined subclass of the white blood cell counted by the blood cell counting apparatus;
preparing a second count result of the predetermined subclass of the white blood cell counted on the basis of the blood cell image;
calculating a difference between the first count result of the blood cell counting apparatus and the second count result of the blood cell image classifying apparatus; and
outputting a quality control screen displaying a difference information showing the difference between the first count result and the second count result.

2. The specimen processing system according to claim 1, wherein the quality control screen displays the difference information in chronological order.

3. The specimen processing system according to claim 1, wherein the difference information is obtained on the basis of a ratio of the difference between the first count result and the second count result to the first count result, or a ratio of the difference between the first count result and the second count result to the second count result.

4. The specimen processing system according to claim 1, wherein the accuracy management screen displays the difference information such that the difference information is compared with information indicating that the difference between the first count result and the second count result is zero.

5. The specimen processing system according to claim 1, wherein the quality control screen is generated on the basis of a plurality of first count results and a plurality of second count results.

6. The specimen processing system according to claim 5, wherein the quality control screen is generated on the basis of an average value of the plurality of the first count results and an average value of the plurality of the second count results.

7. The specimen processing system according to claim 1, wherein the memory stores a selection condition for selecting the first count result and the second count result, and wherein the first count result and the second count result which match the selection condition are used for outputting the quality control screen.

8. A blood cell image classifying apparatus which is configured to be connected to a blood cell counting apparatus configured to count white blood cells for each subclass by measuring a blood specimen flowing in a flow cell, comprising:
an imaging section configured to obtain a blood cell image by imaging a blood smear; and
a controller including a memory under control of a processor, the memory storing instructions enabling the processor to carry out operations, comprising:
receiving a first count result of a predetermined subclass of the white blood cell counted by the blood cell counting apparatus;
preparing a second count result of the predetermined subclass of the white blood cell counted on the basis of the blood cell image;
calculating a difference between the first count result of the blood cell counting apparatus and the second count result of the blood cell image classifying apparatus; and
outputting a quality control screen displaying a difference information showing the difference between the first count result and the second count result, wherein the blood cell counting apparatus comprises an optical detecting section including an optical sensor, and wherein the blood cell image classifying apparatus comprises a microscope unit which comprises an objective lens, an XY stage, and a charge-coupled device (CCD) camera.

9. A specimen processing system comprising:

a blood cell counting apparatus configured to count white blood cells for each subclass by measuring a blood specimen flowing in a flow cell; and a blood cell image classifying apparatus, which is connected to the blood cell counting apparatus so as to perform data communication therewith, and which is configured to count the white blood cells for each subclass on the basis of a blood cell image obtained by imaging a blood smear, wherein the blood cell counting apparatus comprises an optical detecting section including an optical sensor;

wherein the blood cell image classifying apparatus comprises a microscope unit which comprises an objective lens, an XY stage, and a charge-coupled device (CCD) camera, and wherein the blood cell image classifying apparatus further comprises a controller including a memory under control of a processor, the memory storing instructions enabling the processor to carry out operations, comprising:

receiving a first count result of a predetermined subclass of the white blood cell counted by the blood cell counting apparatus;

preparing a second count result of a predetermined subclass of the white blood cell counted on the basis of the blood cell image;

calculating a difference between the first count result of the blood cell counting apparatus and the second count result of the blood cell image classifying apparatus; and outputting a warning when the difference between the first count result and the second count result exceeds a predetermined range.

10. The specimen processing system according to claim 9, wherein the operations further comprise obtaining an initial count result of the predetermined type of the blood cell on the basis of the blood cell image, and wherein the second count result is obtained by changing the initial count result on the basis of an input from a user of the blood cell image classifying apparatus.

11. The specimen processing system according to claim 10, wherein the operations further comprise confirming the second count result, and wherein the comparing operation is performed when the second count result is confirmed.

12. The specimen processing system according to claim 10, wherein the operations further comprise restarting the initial count result to be changed after the warning is output.

13. The specimen processing system according to claim 9, wherein the operations further comprise:

displaying a blood cell image screen which displays the second count result and a blood cell image of a blood specimen corresponding to the second count result in array; and setting the type of the blood cell which is a display object on the blood cell image screen, and wherein the blood cell image screen selectively displays the blood cell image of the blood cell of which the type is set.

14. The specimen processing system according to claim 13, wherein the blood cell image screen displays the first count result, the second count result, and the blood cell image in array.

15. The specimen processing system according to claim 9, wherein the operations further comprise setting the predetermined range relating to the warning.

16. A blood cell image classifying apparatus which is configured to be connected to a blood cell counting apparatus configured to count white blood cells for each subclass by measuring a blood specimen flowing in a flow cell, comprising:

an imaging section configured to obtain a blood cell image by imaging a blood smear; and a controller including a memory under control of a processor, the memory storing instructions enabling the processor to carry out operations, comprising:

counting the blood cells for each type on the basis of the blood cell image which is obtained by imaging the blood smear;

receiving a first count result of a predetermined subclass of the blood cells by the blood cell counting apparatus;

preparing a second count result of the predetermined subclass of the blood cells on the basis of the blood cell image;

calculating a difference between the first count result of the blood cell counting apparatus and the second count result of the blood cell image classifying apparatus; and outputting a warning when the difference between the first count result and the second count result exceeds a predetermined range, wherein the blood cell counting apparatus comprises an optical detecting section including an optical sensor, and wherein the blood cell image classifying apparatus comprises a microscope unit which comprises an objective lens, an XY stage, and a charge-coupled device (CCD) camera.

* * * * *